US009289551B2

(12) United States Patent
Hata et al.

(10) Patent No.: US 9,289,551 B2
(45) Date of Patent: Mar. 22, 2016

(54) PHARMACEUTICAL INJECTION DEVICE

(71) Applicant: PANASONIC HEALTHCARE HOLDINGS CO., LTD., Minato-Ku, Tokyo (JP)

(72) Inventors: Shinsuke Hata, Ehime (JP); Tsuguhiro Kondoh, Ehime (JP); Seiji Kikuchi, Ehime (JP); Toshiaki Iio, Ehime (JP); Yukio Nakajima, Ehime (JP)

(73) Assignee: Panasonic Healthcare Holdings Co., Ltd., Minato-Ku Tokyo (JP)

( * ) Notice: Subject to any disclaimer, the term of this patent is extended or adjusted under 35 U.S.C. 154(b) by 127 days.

(21) Appl. No.: 14/348,896

(22) PCT Filed: Nov. 9, 2012

(86) PCT No.: PCT/JP2012/007216
§ 371 (c)(1),
(2) Date: Apr. 1, 2014

(87) PCT Pub. No.: WO2013/069305
PCT Pub. Date: May 16, 2013

(65) Prior Publication Data
US 2015/0051538 A1 Feb. 19, 2015

(30) Foreign Application Priority Data
Nov. 10, 2011 (JP) ................................ 2011-246767

(51) Int. Cl.
*A61M 5/172* (2006.01)
*A61M 5/20* (2006.01)
(Continued)

(52) U.S. Cl.
CPC ............. *A61M 5/172* (2013.01); *A61M 5/1409* (2013.01); *A61M 5/1452* (2013.01); *A61M 5/20* (2013.01);
(Continued)

(58) Field of Classification Search
CPC ...... A61M 5/1452; A61M 5/172; A61M 5/20; A61M 2205/215; A61M 5/1409; A61M 5/5086; A61M 2205/14; A61M 2005/31588
See application file for complete search history.

(56) References Cited

U.S. PATENT DOCUMENTS 5,989,221 A 11/1999 Hjertman
6,299,601 B1 10/2001 Hjertman
(Continued)

FOREIGN PATENT DOCUMENTS

CN 102123751 A 7/2011
EP 2060284 A1 5/2009
(Continued)

OTHER PUBLICATIONS

Office Action from the corresponding Chinese Patent Application No. 201280039817.9 issued on May 5, 2015.
(Continued)

*Primary Examiner* — Bradley Osinski
(74) *Attorney, Agent, or Firm* — Shinjyu Global IP

(57) ABSTRACT

This pharmaceutical injection device comprises a main body case; a pharmaceutical syringe mounting portion provided inside the main body case; a piston that is provided so as to be movable with respect to a pharmaceutical syringe that is removably attached to the pharmaceutical syringe mounting portion; a drive mechanism for driving the piston; a controller that is electrically connected to the drive mechanism; and an acceleration sensor that is connected to the controller. When a manual mixing mode of the pharmaceutical syringe is selected, the controller changes to the next step (air venting mode) if the inclination angle of the main body case sensed by the acceleration sensor is greater than a specific value.

10 Claims, 24 Drawing Sheets

(51) Int. Cl.
*A61M 5/14* (2006.01)
*A61M 5/145* (2006.01)
*A61M 5/50* (2006.01)
*A61M 5/315* (2006.01)

(52) U.S. Cl.
CPC ... *A61M 5/5086* (2013.01); *A61M 2005/31588* (2013.01); *A61M 2205/14* (2013.01); *A61M 2205/215* (2013.01)

(56) References Cited

U.S. PATENT DOCUMENTS

| | | | |
|---|---|---|---|
| 7,682,155 | B2 | 3/2010 | Raven et al. |
| 8,298,171 | B2 | 10/2012 | Ishikawa et al. |
| 8,556,865 | B2 | 10/2013 | Krulevitch et al. |
| 8,556,866 | B2 | 10/2013 | Krulevitch et al. |
| 8,556,867 | B2 | 10/2013 | Krulevitch et al. |
| 8,679,055 | B2 | 3/2014 | Ishikawa et al. |
| 8,784,381 | B2 * | 7/2014 | Watanabe ............ A61M 5/20 604/154 |
| 2002/0058912 | A1 | 5/2002 | Hjertman |
| 2004/0186424 | A1 | 9/2004 | Hjertman |
| 2005/0209569 | A1 | 9/2005 | Ishikawa et al. |
| 2007/0111175 | A1 | 5/2007 | Raven et al. |
| 2011/0137162 | A1 | 6/2011 | Bruce et al. |
| 2011/0144486 | A1 | 6/2011 | Bruce et al. |
| 2011/0144487 | A1 | 6/2011 | Bruce et al. |
| 2011/0306927 | A1 | 12/2011 | Watanabe et al. |
| 2011/0313349 | A1 | 12/2011 | Krulevitch et al. |
| 2011/0313350 | A1 | 12/2011 | Krulevitch et al. |
| 2011/0313395 | A1 | 12/2011 | Krulevitch et al. |
| 2012/0004637 | A1 | 1/2012 | Krulevitch et al. |
| 2012/0310157 | A1 | 12/2012 | Ishikawa et al. |
| 2014/0148760 | A1 | 5/2014 | Ishikawa et al. |

FOREIGN PATENT DOCUMENTS

| | | |
|---|---|---|
| EP | 2384778 A1 | 11/2011 |
| JP | H11-513586 A | 11/1999 |
| JP | 2009-514605 A | 4/2009 |
| JP | 2009-279438 A | 12/2009 |
| JP | 2010-279793 A | 12/2010 |
| WO | 97/14459 A1 | 4/1997 |
| WO | 02/051471 A1 | 7/2002 |
| WO | 2004/004809 A1 | 1/2004 |
| WO | 2010/098931 A1 | 9/2010 |
| WO | 2010/100883 A1 | 9/2010 |

OTHER PUBLICATIONS

European Search Report from the corresponding European Patent Application No. 12847720.5 issued on Jul. 30, 2015.
International Search Report of PCT Application No. PCT/JP2012/007216.

* cited by examiner

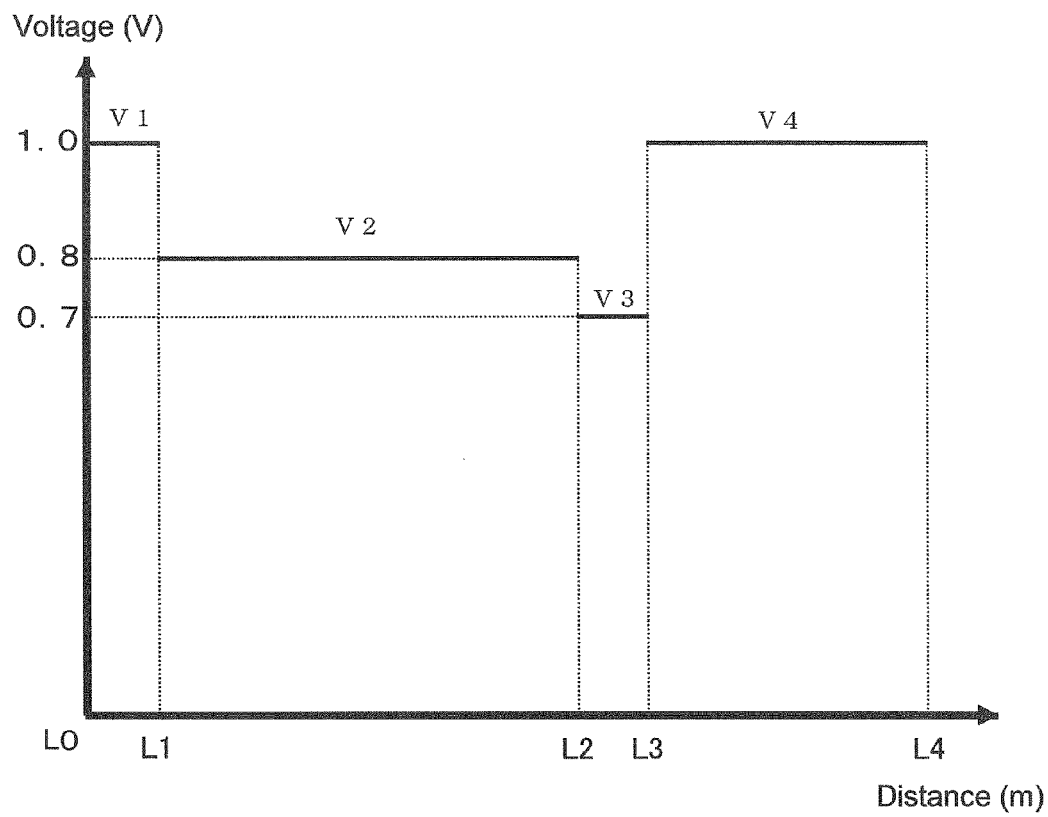

L0: initial position of separation gasket rear end
L1: position when separation gasket rear end touches the bypass
(at the start of dissolution operation)
L2: position when separation gasket rear end touches the push-in gasket
(at the end of dissolution operation)
L3: position of separation gasket distal end after air venting
L4: position of separation gasket distal end after completion of pharmaceutical injection

FIG. 8

PHARMACEUTICAL INJECTION DEVICE

CROSS-REFERENCE TO RELATED APPLICATIONS

This application claims priority to PCT Application No. PCT/JP2012/007216 filed on Nov. 9, 2012, which claims priority to Japanese Application JP2011-246767 filed on Nov. 10, 2011. The entire disclosures of PCT Application No. PCT/JP2012/007216 and Japanese Application JP2011-246767 are hereby incorporated herein by reference.

TECHNICAL FIELD

The present invention relates to a pharmaceutical injection device.

BACKGROUND

A conventional pharmaceutical injection device comprises a main body case having an injection needle insertion and retraction opening, a pharmaceutical syringe mounting portion provided inside this main body case, a pharmaceutical syringe mounted to the pharmaceutical syringe mounting portion, a piston provided movably with respect to the pharmaceutical syringe, a drive mechanism that drives this piston, and a controller that is electrically connected to the drive mechanism.

Also, the pharmaceutical syringe has a cylinder and a push-in gasket that is provided on the rear end side inside the cylinder.

That is, the pharmaceutical can be injected through an injection needle into a body or the like by pressing the push-in gasket with the piston (see Patent Literature 1: Japanese Laid-Open Patent Application 2009-279438, for example).

SUMMARY

However, the following problem was encountered with the conventional pharmaceutical injection device discussed above.

Specifically, with the pharmaceutical injection device disclosed in the above-mentioned publication, the pharmaceutical syringe and the liquid pharmaceutical are housed in a state of being separated inside the pharmaceutical syringe. Prior to pharmaceutical injection, the solid pharmaceutical is dissolved in the liquid pharmaceutical, and the main body case is shaken in this dissolved state to mix the two pharmaceuticals.

Here, mixing the solid pharmaceutical and the liquid pharmaceutical by dissolving the two pharmaceuticals and shaking the main body case in this dissolved state is called the mixing mode, and the mixing operation must be carried out thoroughly before injection.

With a conventional pharmaceutical injection device, however, no means is provided for checking the mixing state in mixing mode. Therefore, there is the risk that pharmaceutical injection will end up being performed in a state in which the mixing operation has not been performed thoroughly.

In view of this, it is an object of the present invention to provide a pharmaceutical injection device with which pharmaceutical injection can be carried out after confirming that the solid pharmaceutical and the liquid pharmaceutical have been thoroughly mixed in the pharmaceutical syringe.

The pharmaceutical injection device pertaining to the present invention comprises a main body case, a pharmaceutical syringe mounting portion, a piston, a drive mechanism, an orientation sensor, and a controller. The main body case has an opening through which an injection needle is inserted and retracted. The pharmaceutical syringe mounting portion is provided inside the main body case, and a pharmaceutical syringe is mounted to it. The piston is provided movably with respect to the pharmaceutical syringe mounted onto the pharmaceutical syringe mounting portion. The drive mechanism drives the piston. The orientation sensor senses the inclination angle of the main body case. The controller is electrically connected to the drive mechanism and the orientation sensor. When manual mixing mode of the pharmaceutical syringe is selected, the controller changes the manual mixing mode to the next mode if the inclination angle of the main body case sensed by the orientation sensor is greater than a specific value.

With the pharmaceutical injection device pertaining to the present invention, when manual mixing mode of the pharmaceutical syringe is selected, the controller changes the manual mixing mode to the next mode if the inclination angle of the main body case sensed by the orientation sensor is greater than a specific value, which allows the device to change to the next step (such as air venting mode) when the main body case is tilted at a sharp angle. As a result, pharmaceutical injection can be performed in a state in which the solid pharmaceutical and the liquid pharmaceutical have been thoroughly mixed inside the pharmaceutical syringe, for example.

BRIEF DESCRIPTION OF DRAWINGS

FIG. 8 is a diagram of the operating state during dissolution with the pharmaceutical injection device in FIG. 1;

DETAILED DESCRIPTION

Embodiments of the present invention will now be described through reference to the appended drawings.

Embodiment 1

Figure 1:
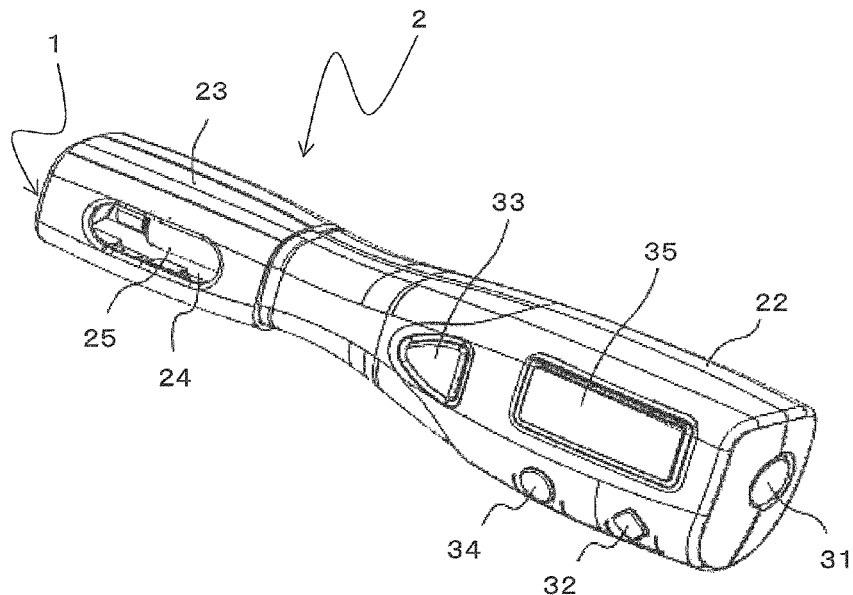
FIG. 1 is an oblique view of the pharmaceutical injection device pertaining to an embodiment of the present invention.
Figure 2:
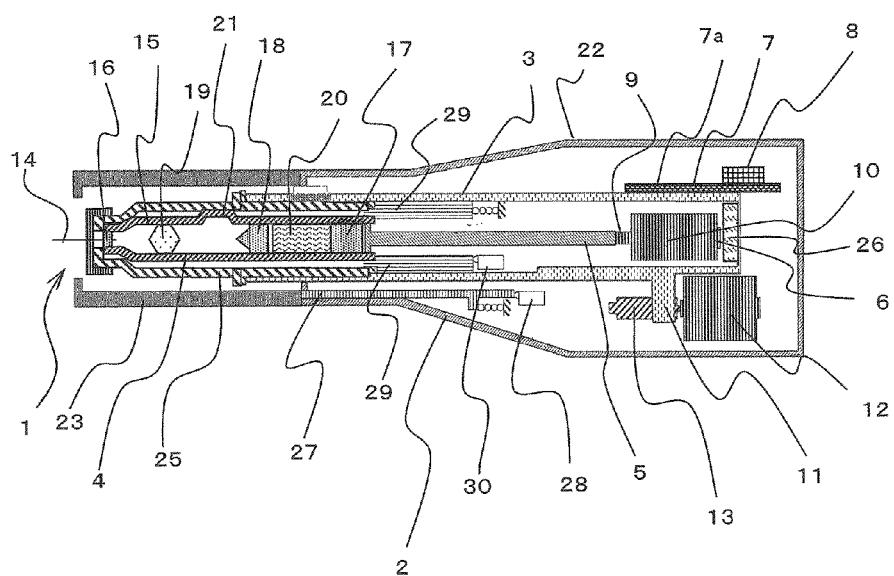
FIG. 2 is a cross section of the pharmaceutical injection device in FIG. 1.

As shown in FIGS. 1 and 2, the pharmaceutical injection device in this embodiment comprises a substantially cylindrical main body case 2 that has an opening 1 on its distal end side through which an injection needle is inserted and retracted; a pharmaceutical syringe mounting portion 3 provided inside the main body case 2; a pharmaceutical syringe 4 that is removably mounted inside the pharmaceutical syringe mounting portion 3; a piston 5 that is provided so as to be movable with respect to the pharmaceutical syringe 4; a drive mechanism 6 for driving the piston 5; a controller 7 that is electrically connected to the drive mechanism 6; and an acceleration sensor (orientation sensor) 8 that is electrically connected to the controller 7.

The acceleration sensor 8 is provided in order to sense the acceleration produced when the main body case 2 is shaken or tilted, and is mounted on a substrate 7a having the controller 7. The substrate 7a is installed so as to be parallel to the drive direction of the piston 5.

The drive mechanism 6 includes a bolt 9 inserted into a rear end opening in the piston 5, and a piston drive motor 10 for driving the bolt 9. Specifically, when the piston drive motor 10 is rotated in a first direction, the bolt 9 pushes out the piston 5 to the opening 1. Conversely, when the piston drive motor 10 is rotated in a second direction that is the opposite of the first direction, the piston 5 can be pulled back toward the piston drive motor 10.

The piston drive motor 10 and the piston 5 are disposed along with the pharmaceutical syringe 4 inside the pharmaceutical syringe mounting portion 3. Female threads 11 are provided toward the outside of the rear end of the pharmaceutical syringe mounting portion 3. A bolt 13 of a needle insertion and retraction drive motor 12 meshes with these female threads 11. That is, when the needle insertion and retraction drive motor 12 is driven, the female threads 11 and the bolt 13 mesh, causing the pharmaceutical syringe mounting portion 3 to move back and forth with respect to the opening 1. This causes the distal end of an injection needle 14 provided on the distal end side of the pharmaceutical syringe 4 to move in or out through the opening 1.

Figure 9:
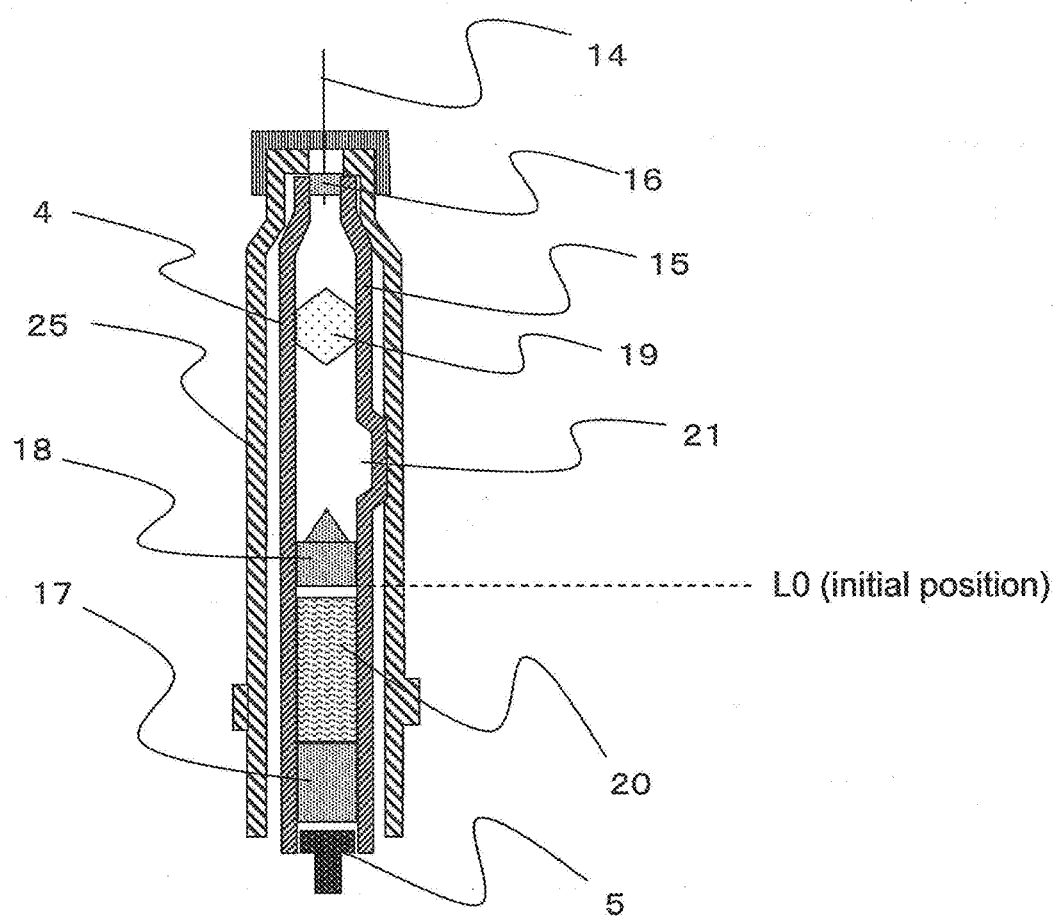
FIG. 9 is a cross section of the operating state during dissolution with the pharmaceutical injection device in FIG. 1.

As shown in FIG. 9, the pharmaceutical syringe 4 has a cylindrical cylinder 15, a distal end gasket 16 provided on the distal end side inside this cylinder 15, a push-in gasket 17 provided on the rear end side inside the cylinder 15, a separation gasket 18 provided in the middle inside the cylinder 15, a solid pharmaceutical 19 contained inside the cylinder 15 between the distal end gasket 16 and the separation gasket 18, a liquid pharmaceutical 20 contained inside the cylinder 15 between the push-in gasket 17 and the separation gasket 18, and a bypass 21 that protrudes in the outer peripheral direction of the cylinder 15 at the portion of the cylinder 15 between the distal end gasket 16 and the separation gasket 18. The controller 7 is configured such that after the orientation of the main body case 2 has been sensed by the acceleration sensor 8, the drive mechanism 6 causes the piston 5 to press the push-in gasket 17 to the distal end gasket 16 side.

Also, the rate at which the push-in gasket 17 is pushed in by the piston 5 is set so that if we let V1 be the push-in rate when the separation gasket 18 reaches the bypass 21, V2 be the push-in rate at the point when the separation gasket 18 goes through the bypass 21, V3 be the push-in rate at the point when air is vented after the separation gasket 18 has gone through the bypass 21, and V4 be the push-in rate at the point when a pharmaceutical is injected after air venting, the push-in rate V2 will be lower than the push-in rate V1.

Returning to FIGS. 1 and 2, the main body case 2 has a housing 22 and a distal end cap 23 on the distal end side of the housing 22.

The distal end cap 23 is removably mounted to the housing 22. A window 24 is provided on the outer peripheral part of the distal end cap 23.

After the pharmaceutical syringe 4 has been mounted inside the pharmaceutical syringe mounting portion 3, the outer periphery of the pharmaceutical syringe 4 is covered by a syringe cover 25 (see FIG. 9). In this state, the injection needle 14 is mounted to the distal end gasket 16 on the distal end side of the pharmaceutical syringe 4.

When the piston 5 pushes the push-in gasket 17 forward, the liquid pharmaceutical 20 goes through the bypass 21 and flows to the solid pharmaceutical 19 side. When the push-in gasket 17 moves farther forward, the pharmaceutical mixture flows out of the injection needle 14.

The rotation of the piston drive motor 10 is detected by an encoder 26. Consequently, the amount by which the piston 5 protrudes is sensed. The solid pharmaceutical 19 and the liquid pharmaceutical 20 contained inside the pharmaceutical syringe 4 are put in at a pharmaceutical company, etc.

The housing 22 of the main body case 2 also houses a number of switches. More specifically, a distal end cap detector switch 28 is disposed at the rear end of a control rod 27 provided around the outer periphery of the pharmaceutical syringe mounting portion 3. When the distal end cap 23 is mounted to the distal end of the housing 22, the control rod 27 is pushed rearward. Consequently, the distal end cap detector switch 28 detects that the distal end cap 23 has been mounted.

A control rod 29 is also disposed inside the pharmaceutical syringe mounting portion 3. When the control rod 29 is pushed rearward by the syringe cover 25, a syringe cover detector switch 30 detects whether or not the syringe cover 25 has been mounted.

The acceleration sensor 8 is mounted on the substrate 7a having the controller 7. The substrate 7a is installed so as to be parallel to the drive direction of the piston 5, which allows acceleration with respect to the main body case 2 to be sensed more favorably. In this embodiment, the substrate 7a is disposed parallel to the drive direction of the piston 5, but may instead be installed perpendicular to the drive direction of the piston 5.

Returning to FIG. 1, various control buttons and so forth are provided to the outer periphery of the housing 22 of the main body case 2. More specifically, a power button 31 is provided to the rear end of the housing 22. A dissolution button 32, a pharmaceutical injection button 33, an end button 34, and a display section 35 are provided to the outer periphery of the housing 22.

Figure 3:
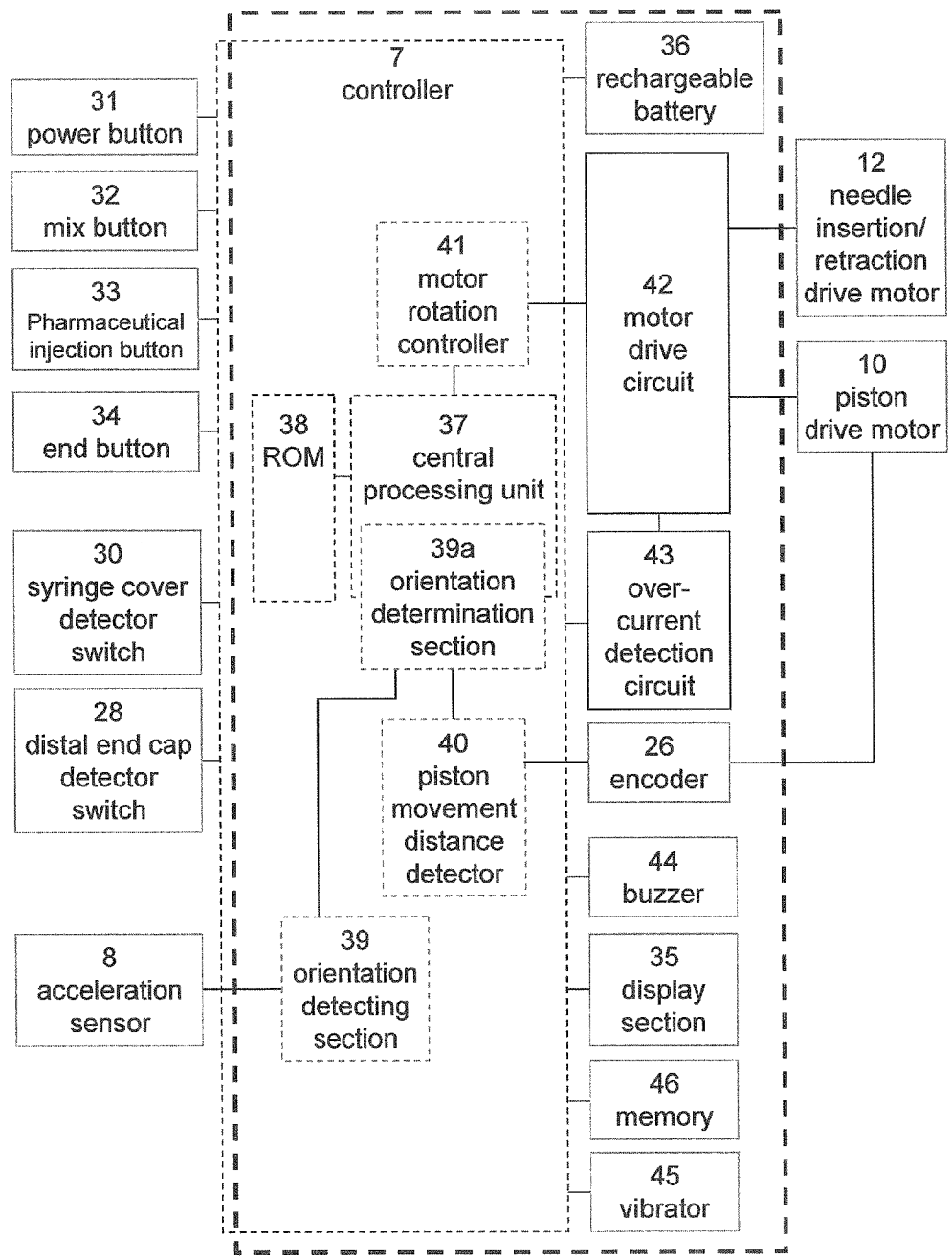
FIG. 3 is a control block diagram of the simplified electrical configuration of the pharmaceutical injection device in FIG. 1.

FIG. 3 is an electrical block diagram.

The controller 7 is constituted by a microprocessor. The rechargeable battery 36 shown in FIG. 3 is connected to the controller 7 and other electrically driven parts. The electrical connection state of the rechargeable battery 36 and the other electrically driven parts is not shown, to keep FIG. 3 from being too complicated.

A central processing unit 37 is provided inside the controller 7. The central processing unit 37 performs operational control over the various blocks shown in FIG. 3. A program that performs this operational control is written into a ROM 38. An orientation detecting section 39, a piston movement distance sensor 40, and a motor rotation controller 41 are connected to the central processing unit 37.

An orientation determination section 39a and the acceleration sensor 8 are connected to the orientation detecting section 39. The orientation sensing result from the acceleration sensor 8 is converted into information for determining the orientation at the orientation determination section 39a. The orientation determination section 39a performs various kinds of operational control according to the orientation, such as using the orientation information obtained from the orientation detecting section 39 to compare the inclination sensed by the acceleration sensor 8 with a preset value, determine whether or not to drive the piston drive motor 10, and so forth.

The piston movement distance detector 40 is connected to the encoder 26. The encoder 26 is attached to the piston drive motor 10, and the movement distance of the piston 5 is detected by detecting the rotation of the piston drive motor 10.

The motor rotation controller 41 is connected to a motor drive circuit 42. The motor rotation controller 41 is configured such that when the value detected by the piston movement distance detector 40 reaches a preset value, the motor drive circuit 42 is controlled to change the movement speed of the piston 5.

The piston drive motor 10 and the needle insertion and retraction drive motor 12 are connected to the motor drive circuit 42. The motor drive circuit 42 is connected to an over-current detection circuit 43.

The motor drive circuit 42 is controlled by the motor rotation controller 41, and drives the piston drive motor 10 and the needle insertion and retraction drive motor 12.

The over-current detection circuit 43 is a circuit that detects the amount of current from the motor drive circuit 42, and detects malfunction of the motors.

The controller 7 is also connected to a buzzer 44 for issuing a caution and to a vibrator 45 that gives notification by vibrating, so as to alert the user to the usage status of the pharmaceutical injection device.

The controller 7 is also connected to the display section 35, which displays cautions and information for operating the pharmaceutical injection device, and to a memory 46 for recording various kinds of data.

Figure 4:
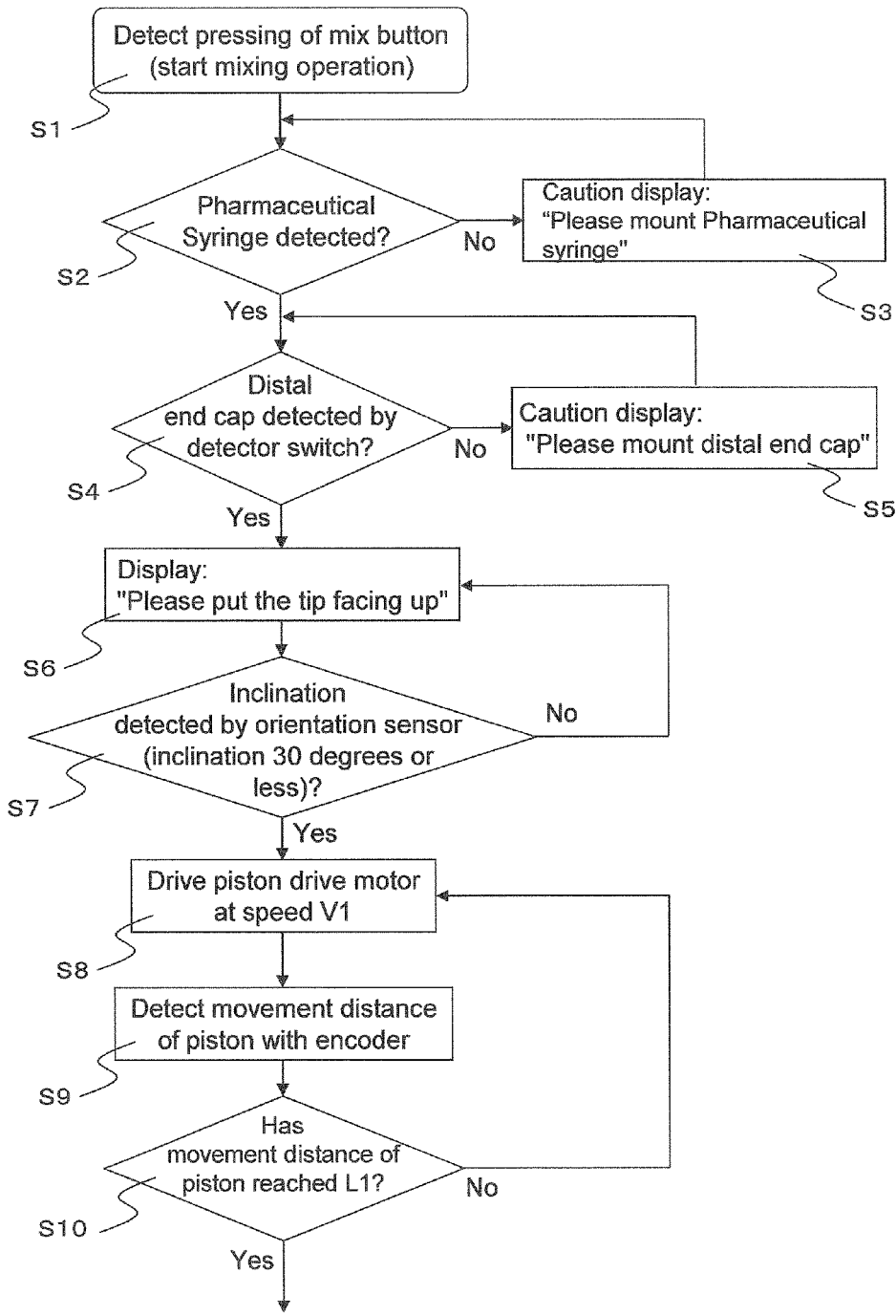
FIG. 4 is a flowchart of the operational control of the pharmaceutical injection device in FIG. 1.

The operation with the above configuration will now be described through reference to the operational flowchart shown in FIG. 4.

First, as shown in S1, the dissolution button 32 is pressed (see FIG. 1).

Then, in S2, the syringe cover detector switch 30 detects whether or not the syringe cover 25 has been mounted, and thereby detects the mounting of the pharmaceutical syringe 4. If the syringe cover 25 has not been mounted, a caution display of "Please mount pharmaceutical syringe (syringe cover)" is given on the display section 35 (see FIG. 1), as shown in S3.

Once the mounting of the syringe cover 25 has been confirmed, the distal end cap detector switch 28 checks whether or not the distal end cap 23 has been mounted, as shown in S4. Here again, as shown in S5, if the distal end cap 23 has not been mounted, a caution display of "Please mount distal end cap" is given on the display section 35.

The following operation is not performed if the syringe cover 25 and the distal end cap 23 have been determined in S2 and S4 not to have been mounted.

Once it has been confirmed in S2 and S4 that the syringe cover 25 and the distal end cap 23 have been mounted, a display of "Please put the tip facing up" is left on the display section 35 as shown in S6 for a specific length of time.

In S7, the inclination of the main body case 2 is sensed by the acceleration sensor 8. Hereinafter, the inclination will be referred to by using the direction perpendicular to the horizontal plane as zero degrees. If the inclination of the main body case 2 exceeds a specific value (the set value), the operation is stopped until the inclination falls back to within the specific value (the set value), and operation is restarted once the inclination has been within the specific value for a specific length of time. When leakage from the injection needle 14 is taken into account, it is preferable for the inclination at which operation is performed to be 30 degrees or less.

Although not discussed in detail here, the inclination of the main body case 2 is continuously sensed by the acceleration sensor 8 during the operation from S7 (FIG. 4) onward (S26).

If the inclination of the main body case 2 exceeds a specific angle (such as ±30 degrees with respect to the vertical direction) (S27), the piston drive motor 10 is stopped (S28), and a caution display of "Main body case is tilted too far. Operation has been stopped" (S29) and "Please put the tip facing up" (S30) are given on the display section 35. This prompts the user not to tilt the main body case 2 so far that the inclination of the main body case 2 exceeds a specific angle (such as ±30 degrees with respect to the vertical direction). S31 is a loop with S30, and is used to confirm that the inclination of the main body case 2 has exceeded the specific angle (such as ±30 degrees with respect to the vertical direction).

In S32, once the inclination is sensed to be at or under the specific angle (such as ±30 degrees with respect to the vertical direction), the operation prior to the stoppage is restarted, and the flow returns to S8.

In S8, as shown in FIG. 9, the piston drive motor 10 is driven from its initial state prior to the mixing operation, at a speed V1 (push-in rate V1).

In S9, the movement distance of the piston 5 is calculated by the encoder 26 during drive of the piston 5.

Figure 10:
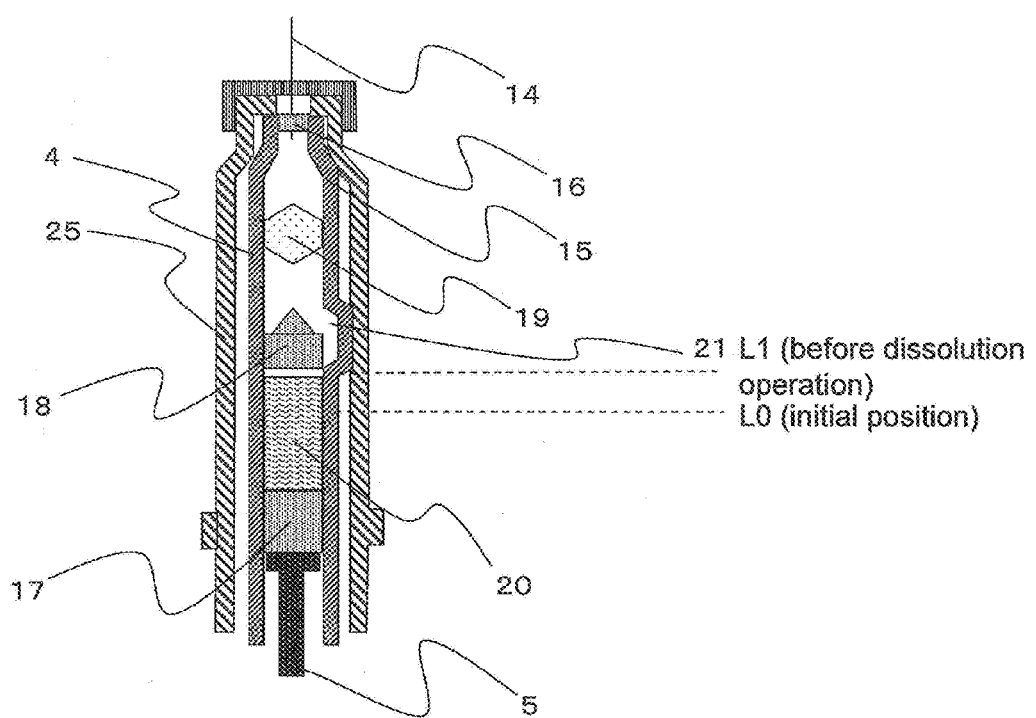
FIG. 10 is a cross section of the operating state during dissolution with the pharmaceutical injection device in FIG. 1.

In S10, the piston drive motor 10 continues to move at the speed V1 (the push-in rate V1) until the rear end of the separation gasket 18 goes from L0 in FIG. 10 (the initial position) to the position L1 a specific distance away. As shown in FIG. 10, L1 indicates the position where the rear end of the separation gasket 18 touches the bypass 21. Thus, it is position information about the movement distance from L0 to L1, that is, until the rear end of the separation gasket 18 changes from its initial state to a contact state. This L1 position information is stored ahead of time in the memory 46.

When the rear end position of the separation gasket 18 reaches the L1 position, the dissolution operation commences. Then, as shown in S11 in FIG. 5, the push-in rate V2 of the separation gasket 18 by the piston drive motor 10 is switched so as to be lower than the push-in rate V1 (V2<V1).

Figure 11:
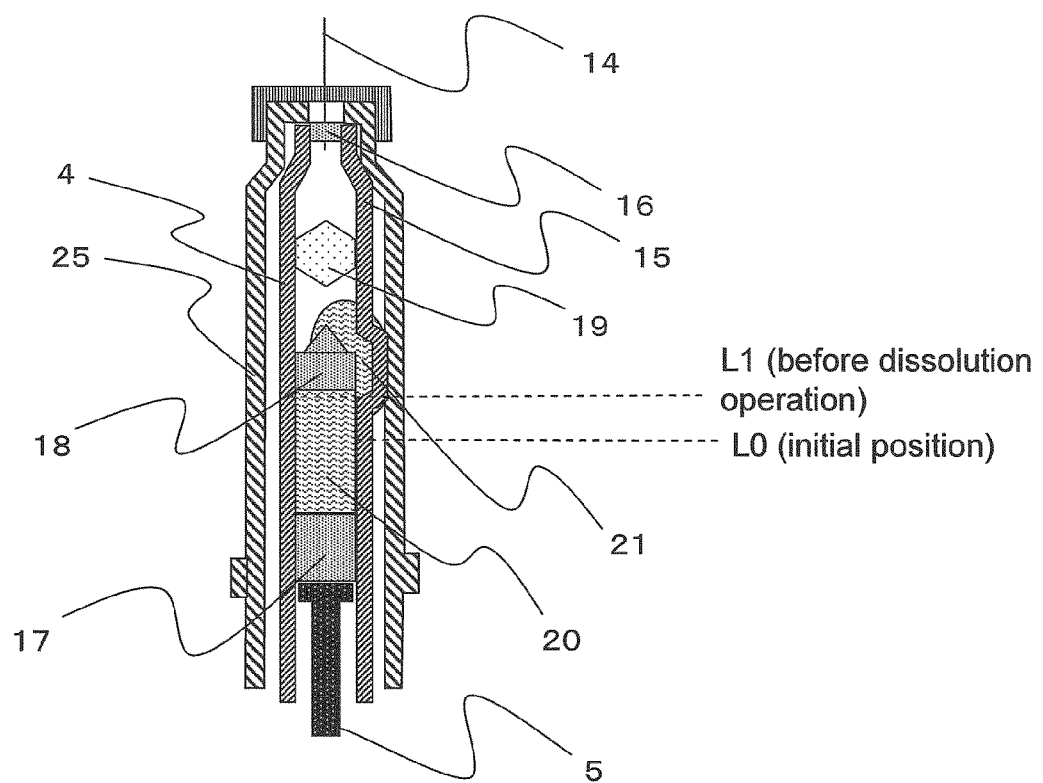
FIG. 11 is a cross section of the operating state during dissolution with the pharmaceutical injection device in FIG. 1.

As shown in FIG. 11, when the rear end of the separation gasket 18 starts to pass through the bypass 21, the liquid pharmaceutical 20 begins to flow through the bypass 21 to the solid pharmaceutical 19 side.

Figure 12:
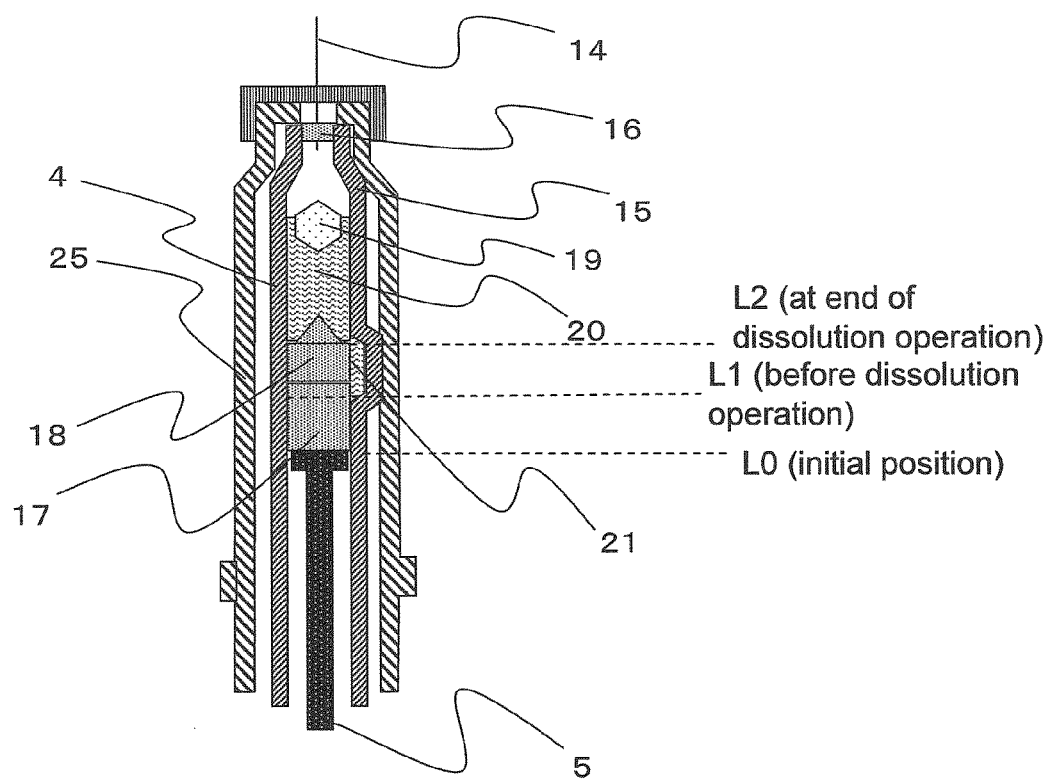
FIG. 12 is a cross section of the operating state during dissolution with the pharmaceutical injection device in FIG. 1.

Then, in S12, the piston drive motor 10 continues to move at the speed V2 (the push-in rate V2) until the distal end of the separation gasket 18 reaches L2 in FIG. 12. The movement distance from L1 to L2, as shown in FIG. 12, is the movement distance up until the separation gasket 18 and the push-in gasket 17 come into contact, that is, it is the movement distance until the separation gasket 18 goes from its initial state to a state of being in contact with the push-in gasket 17. This L2 position information is stored ahead of time in the memory 46.

Because the push-in rate V2 of the separation gasket 18 by the piston drive motor 10 is thus set to be lower than the push-in rate V1, it is less likely that there will be a sudden surge in pressure on the solid pharmaceutical 19 side when the liquid pharmaceutical 20 passes through the bypass 21. As a result, this prevents some of the liquid pharmaceutical from squirting out of the distal end of the injection needle 14 mounted to the distal end gasket 16 of the cylinder 15, or from overflowing more than necessary. That is, liquid leakage from the distal end of the injection needle 14 can also be prevented during pharmaceutical dissolution, so the dissolution operation can be carried out more favorably.

Figure 5:
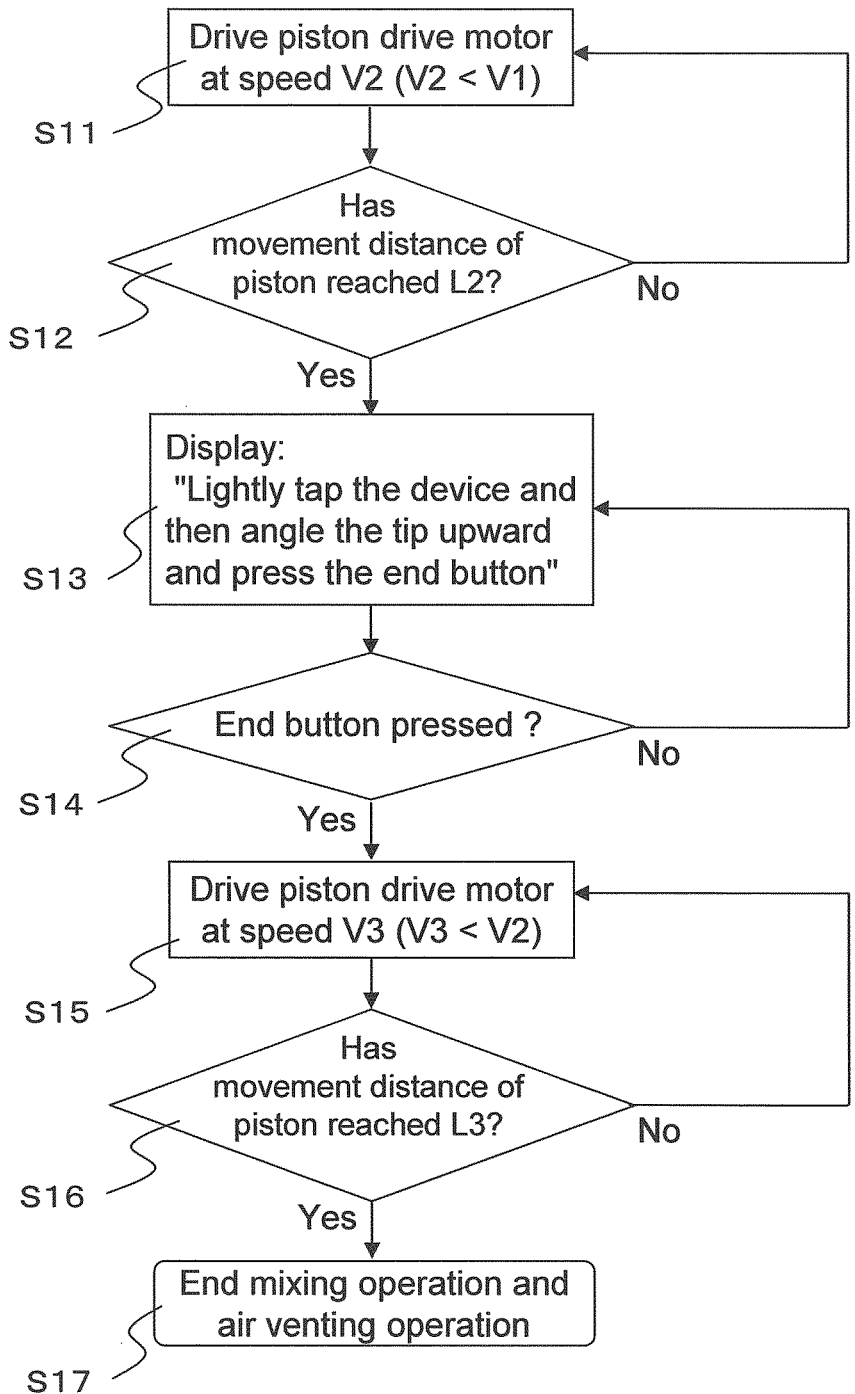
FIG. 5 is a flowchart of the operational control of the pharmaceutical injection device in FIG. 1.

Next, as shown in FIG. 12, when the distal end position of the separation gasket 18 reaches L2, the display section 35 displays "Slowly shake the device and then angle the tip upward and press the end button" as shown in S13 in FIG. 5, and the operation of the piston drive motor 10 is temporarily stopped.

In the state shown in FIG. 12, the user shakes the main body case 2 to thoroughly mix the solid pharmaceutical 19 and the liquid pharmaceutical 20 inside the pharmaceutical syringe 4. This operation is called the manual mixing mode. This point will be described in detail through reference to FIGS. 15 and 16.

Going back to the description of the operation from FIG. 12 onward, based on the above-mentioned display ("Then angle the tip upward and press the end button"), in S14 in FIG. 5, when the end button 34 shown in FIG. 1 is pressed, operation begins in air venting mode.

In operation in air venting mode, while tilting is sensed by the acceleration sensor 8, the push-in rate V3 of the separation gasket 18 by the piston drive motor 10 is switched to be lower than the push-in rate V1 (V3<V1). More preferably, the push-in rate V3 is set lower than the push-in rate V2 (V3<V2) as in this embodiment.

Since liquid is most likely to leak out from the distal end of the injection needle 14 during operation in air venting mode, the speed at which the piston 5 is moved is further reduced (S15).

Figure 13:
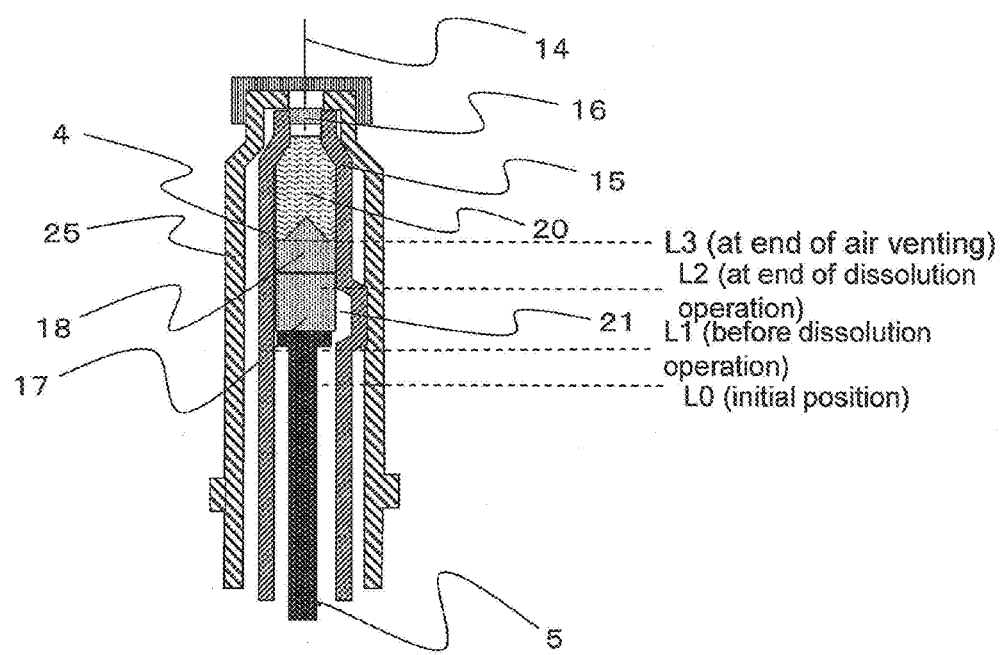
FIG. 13 is a cross section of the operating state during dissolution with the pharmaceutical injection device in FIG. 1.

Then, in S16, the piston drive motor 10 is operated at the speed V3 (the push-in rate V3) until the distal end position of the separation gasket 18 reaches L3. The movement distance from L2 to L3, as shown in FIG. 13, indicates the position after the separation gasket 18 and the push-in gasket 17 have passed through the bypass 21 in a state of being in contact with each other. The L3 position information is stored ahead of time in the memory 46.

As shown in S17, the air venting operation is ended when the distal end position of the separation gasket 18 reaches L3.

Figure 6:
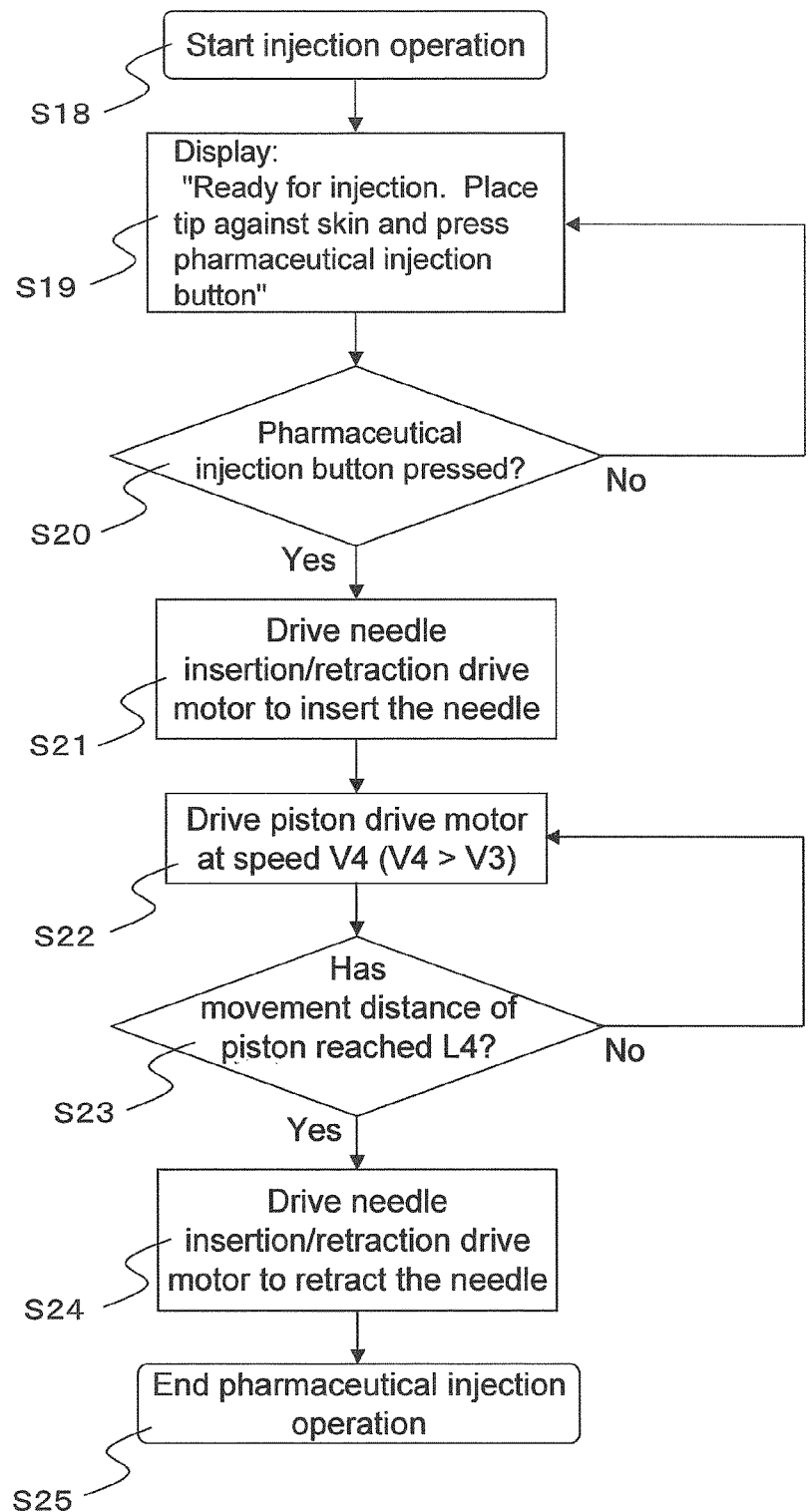
FIG. 6 is a flowchart of the operational control of the pharmaceutical injection device in FIG. 1.
Figure 7:
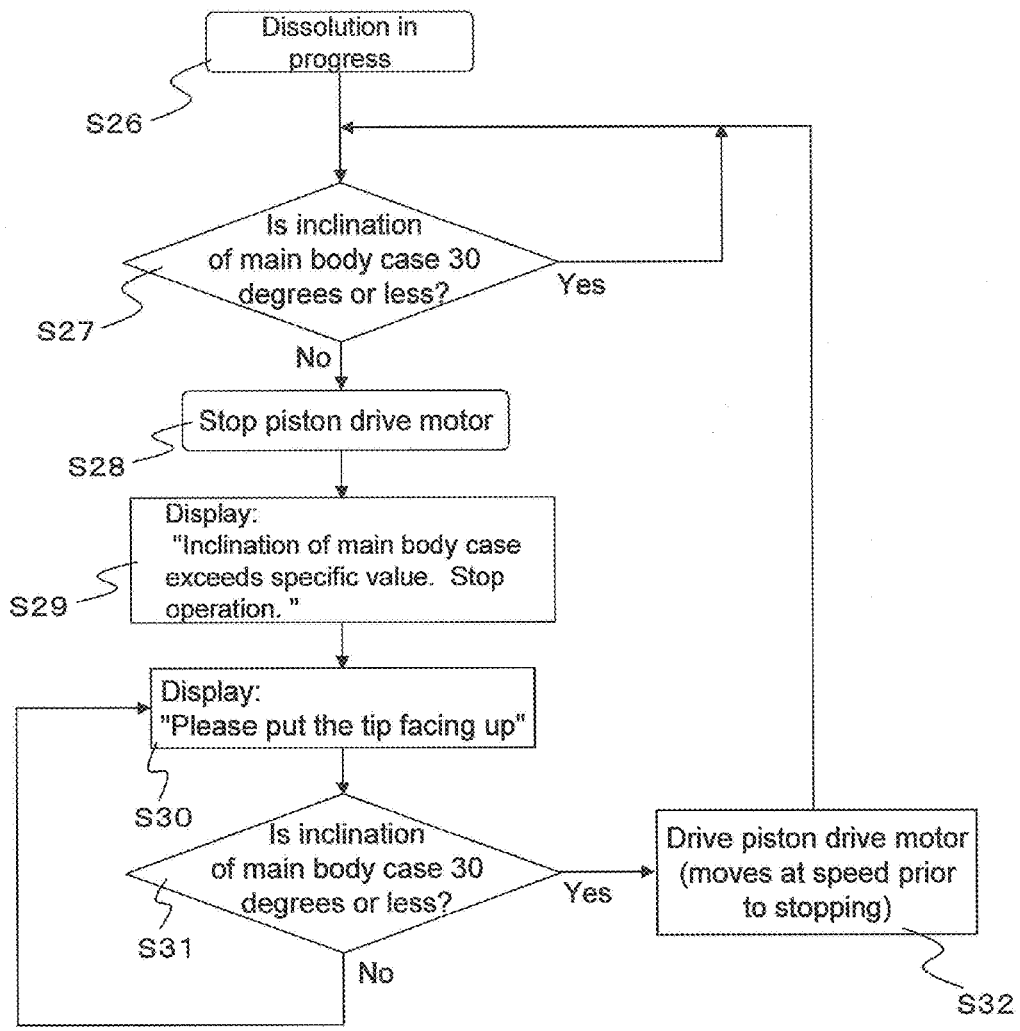
FIG. 7 is a flowchart of the operational control of the pharmaceutical injection device in FIG. 1.

The pharmaceutical injection operation is then commenced in S18 as shown in FIG. 6.

When the automatic dissolution, manual mixing, and air venting operations discussed above are complete, in S19 the display section 35 in FIG. 1 displays a message of "Ready for injection. Place tip against skin and press pharmaceutical injection button," and the operation of the piston drive motor 10 is temporarily stopped.

Then, in S20, the operation of piercing the skin is commenced when it is detected that the pharmaceutical injection button 33 shown in FIG. 1 has been pressed.

In S21, the needle insertion operation is accomplished by moving the needle insertion and retraction drive motor 12. This "needle insertion operation" refers to an operation of driving the needle insertion and retraction drive motor 12 to move the pharmaceutical syringe mounting portion 3 to the opening 1 side, and thereby causing the injection needle 14 to stick out from the opening 1.

At this point, the opening 1 is already being pressed against the site on the body where the injection is to be made. Therefore, the injection needle 14 is moved toward the body, the injection needle 14 is plunged into the body, and the preparatory operation (needle insertion operation) prior to pharmaceutical injection is complete.

Then, when the preparatory operation (needle insertion operation) prior to pharmaceutical injection is complete, in S22 the operation of pharmaceutical injection is commenced.

In the pharmaceutical injection operation, the push-in rate of the separation gasket by the piston drive motor 10 is switched to the rate V4 so as to be higher than the push-in rate V3 (V4>V3).

Since it is unlikely that there will be leakage from the distal end of the injection needle during the pharmaceutical injection operation, the speed at which the piston 5 is moved can be increased.

Then, in S23, the piston drive motor 10 continues to move at the speed V4 (the push-in rate V4) until the distal end position of the separation gasket 18 reaches L4.

Figure 14:
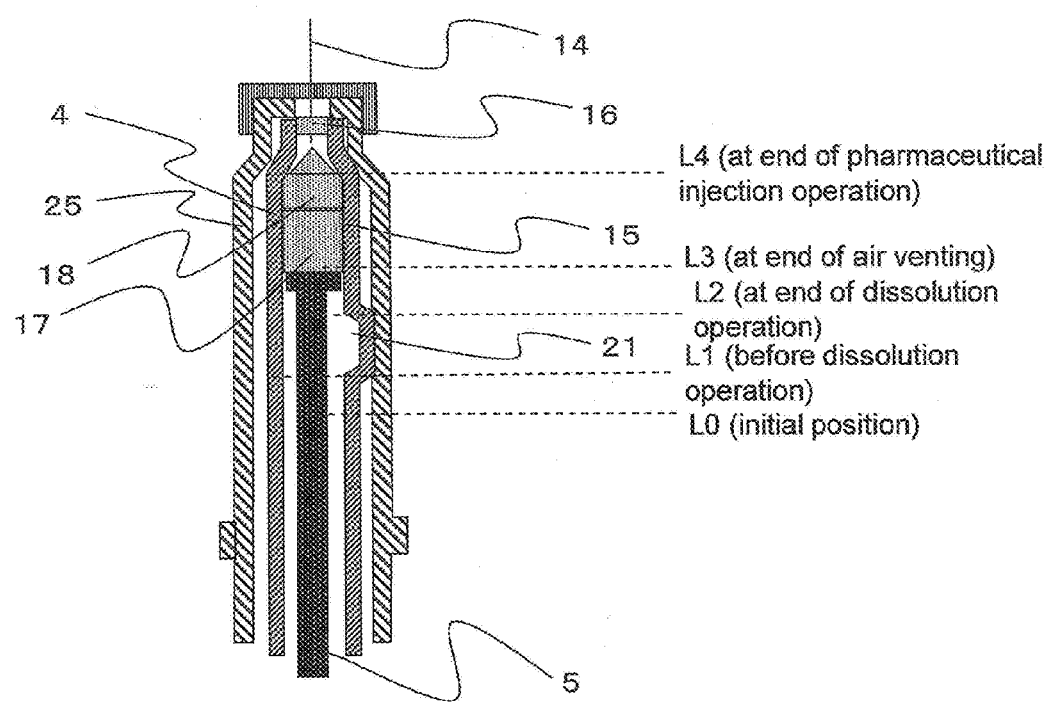
FIG. 14 is a cross section of the operating state during dissolution with the pharmaceutical injection device in FIG. 1.

As shown in FIG. 14, the movement distance from L3 to L4 indicates the position up to where the separation gasket 18 reaches the inclined portion of the distal end of the pharmaceutical syringe 4. Position information about this movement distance L4 is stored ahead of time in the memory 46.

Finally, when the distal end position of the separation gasket 18 reaches L4, the needle retraction operation is commenced. More specifically, in the needle retraction operation in S24, the piston drive motor 10 is stopped and the needle insertion and retraction drive motor 12 is moved.

This needle retraction operation involves driving the needle insertion and retraction drive motor 12 to move the pharmaceutical syringe mounting portion 3 to the rear end side, and thereby stowing the injection needle 14 inside the opening 1.

After this, in S25, when the pharmaceutical syringe mounting portion 3 reaches its initial position prior to the needle insertion operation, the needle retraction operation is complete, and the operation of pharmaceutical injection into the body is ended.

FIG. 8 is a graph of the operating state during dissolution with this pharmaceutical injection device. The vertical axis is the applied voltage (value) to a motor driver (not shown) for driving the piston drive motor 10, and the horizontal axis is the rear end position or distal end position of the separation gasket 18, showing a simulation of the flow of the operation at the above-mentioned push-in rates (V1, V2, V3, and V4).

Although not discussed in detail here, the voltage values of a piston speed control signal are varied (such as 1.0 volt for V1 and V4, 0.8 volt for V2, and 0.7 volt for V3), so that as the piston 5 moves, the push-in rate V2 when the liquid pharmaceutical 20 passes through the bypass 21 is lower than the initial push-in rate V1. The push-in rate V3 during air venting is lower than the push-in rate V2. Further, the push-in rate V4 during pharmaceutical injection is higher than the push-in rate V3.

FIG. 8 is just one example of an embodiment, and a standby period for user manipulation selection can be allocated as needed, such as between V2 and V3, or between V3 and V4. In this case the dissolution operation can be temporarily stopped so that the various speeds are all zero. This is generally how the settings are made.

In the above description, position information about L0, L1, L2, L3, and L4 indicated the distal end position or rear end position of the separation gasket 18, but may be controlled with the movement distance of the piston 5.

As discussed above, the pharmaceutical injection device in this embodiment is such that in the pharmaceutical dissolution operation, the push-in rate V2 at the point when the separation gasket 18 passes through the bypass 21 is set lower than the push-in rate V1 when the separation gasket 18 is pushed in until it comes into contact with the bypass 21. Consequently, the liquid pharmaceutical 20 flows gently through the bypass 21 to the solid pharmaceutical 19 side. As a result, leakage from the distal end gasket 16 side can be reduced during pharmaceutical dissolution. Thus, the surroundings can be kept clean, without the pharmaceutical splashing onto the surrounding area when the pharmaceutical injection device is operated by the user, and the automatic pharmaceutical dissolution can be carried out easily and safely.

The basic configuration and operation in this embodiment will be understood from the above description, and the most salient features of this embodiment will now be described.

As shown in FIG. 12, the pharmaceutical injection device in this embodiment has a manual mixing mode in which the solid pharmaceutical 19 and the liquid pharmaceutical 20 are manually mixed inside the pharmaceutical syringe 4.

Figure 15:
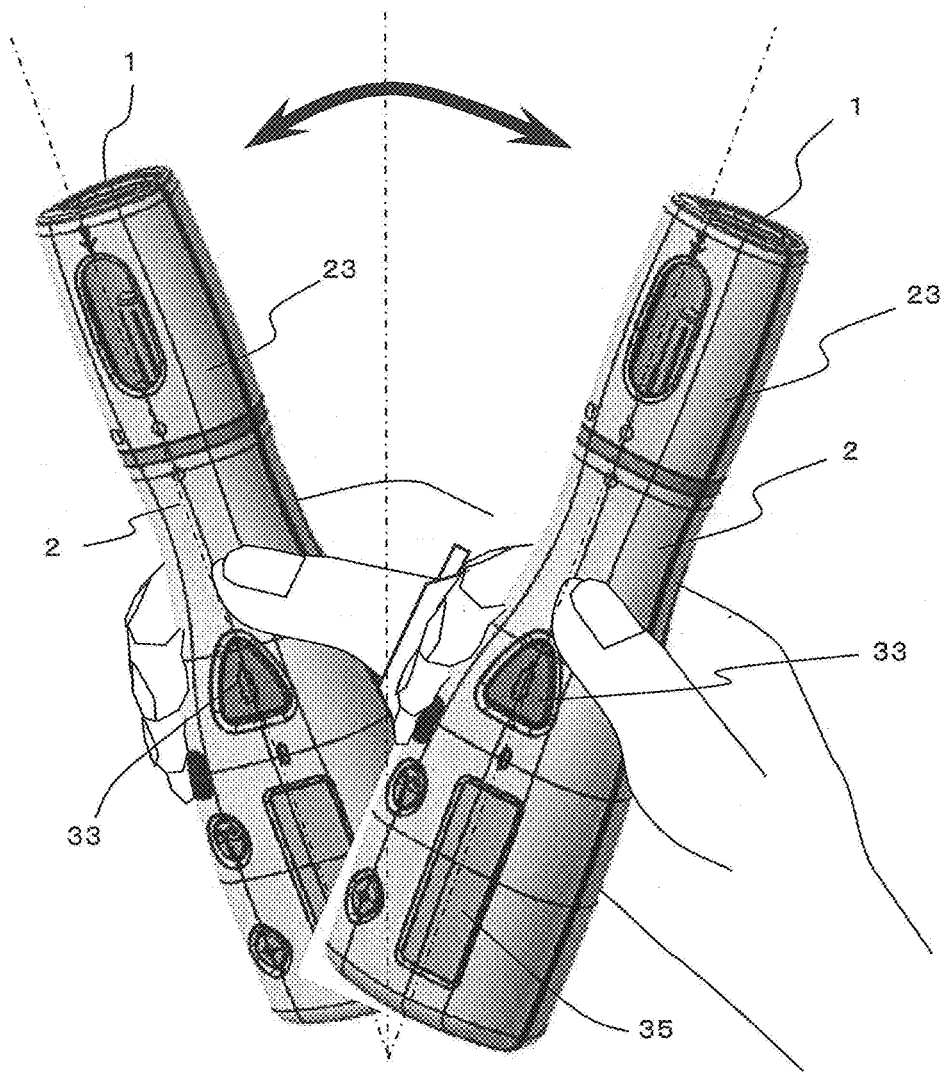
FIG. 15 is a diagram of the shaking state in manual mixing mode with the pharmaceutical injection device in FIG. 1.

As shown in FIG. 15, in the manual mixing mode, the main body case 2 is gently shaken at an angle that is greater than a specific angle (such as an angle greater than 30 degrees) with respect to the vertical axis.

Figure 16:
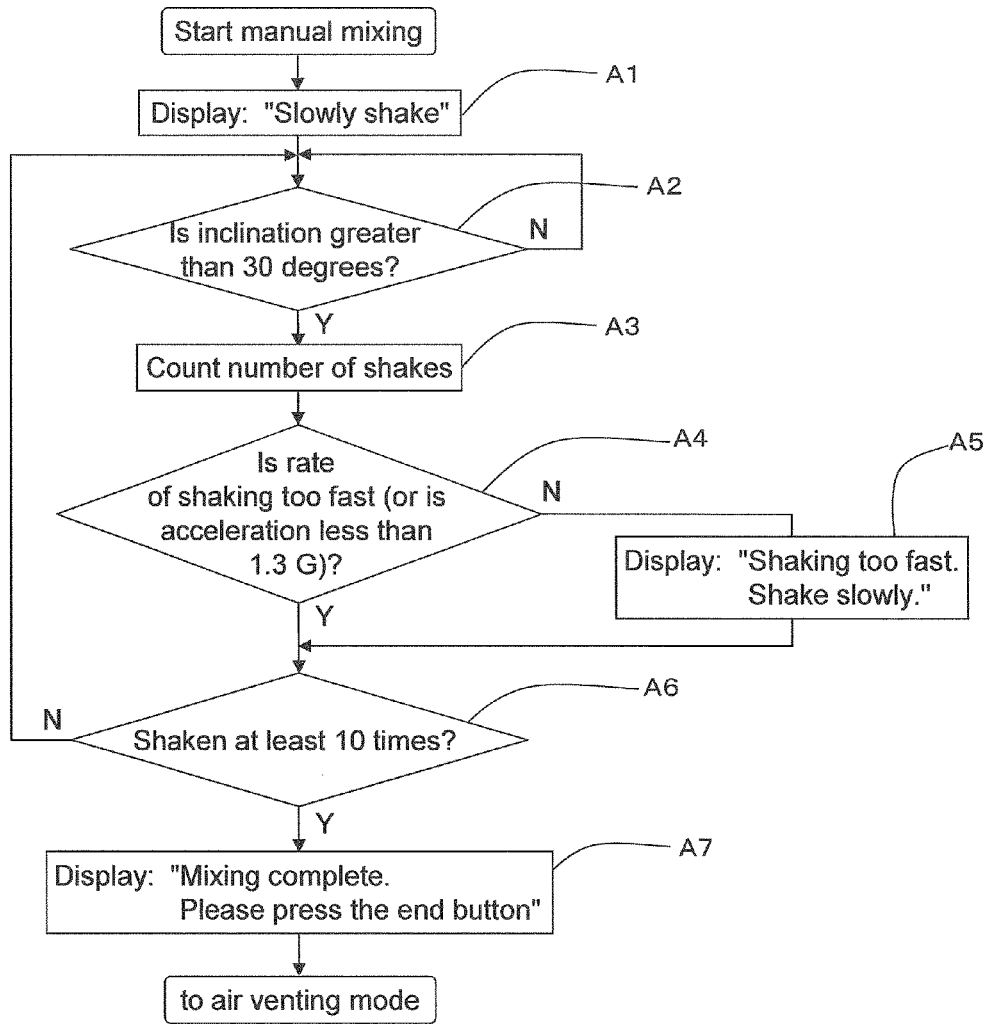
FIG. 16 is a flowchart of the manual mixing mode of the pharmaceutical injection device in FIG. 1.

FIG. 16 is a flowchart of the flow from the start of the manual mixing mode until the subsequent air venting mode.

First, prior to the manual mixing mode, as discussed above, a message of "Slowly shake the device and then angle the tip upward and press the end button" is displayed on the display section 35 (step A1).

Therefore, as shown in FIG. 15, the user shakes the main body case 2, and at this point the acceleration sensor 8 of the pharmaceutical injection device senses the amount of shaking (the shake angle (inclination of the main body case 2)).

More specifically, the orientation detecting section 39 senses the number of degrees of shake angle (inclination of the main body case 2) sensed by the acceleration sensor 8. The orientation determination section 39a then determines whether or not the angle sensed by the acceleration sensor 8 is greater than a specific value (such as 30 degrees) (step A2).

The orientation determination section 39a also counts the number of times the main body case 2 is shaken at an angle greater than the specific value (step A3).

In this embodiment, since the acceleration sensor 8 is used as an orientation sensor, the acceleration generated during the shaking of the main body case 2 can also be sensed.

More specifically, with the pharmaceutical injection device in this embodiment, it is detected whether or not the acceleration generated in the shaking of the main body case 2 is less than a specific value (such as 1.3 G) (step A4).

If the acceleration is at or above the specific value, a message of "Shaking too fast. Shake slowly" is displayed on the display section 35 (step A5).

If the acceleration is less than the specific value, the orientation determination section 39a determines whether or not the number of shakes is at or over a specific number (such as 10 times) (step A6).

If the number of times here is at or above a specific number (such as 10 times), and the main body case 2 has been shaken at an angle that is greater than a specific angle, the orientation determination section 39a causes the display section 35 to display a message of "Mixing complete. Please press the end button" (step A7).

The above operation results in the proper mixing of the solid pharmaceutical 19 and the liquid pharmaceutical 20 inside the pharmaceutical syringe 4.

Therefore, when the user presses the end button 34 on the basis of the display in step A7, the air venting mode is executed as discussed above and as shown in FIGS. 12 and 13.

Embodiment 2

The basic operation of the pharmaceutical injection device pertaining to another embodiment of the present invention will now be described through reference to FIGS. 17a to 18b.

The pharmaceutical injection device in this embodiment is what is known as a full-auto injector, and the confirmation of pharmaceutical syringe mounting, the air venting operation, and the pharmaceutical injection operation are carried out according to the flowcharts shown in FIGS. 17a to 18b.

Figures 17A, 17B:
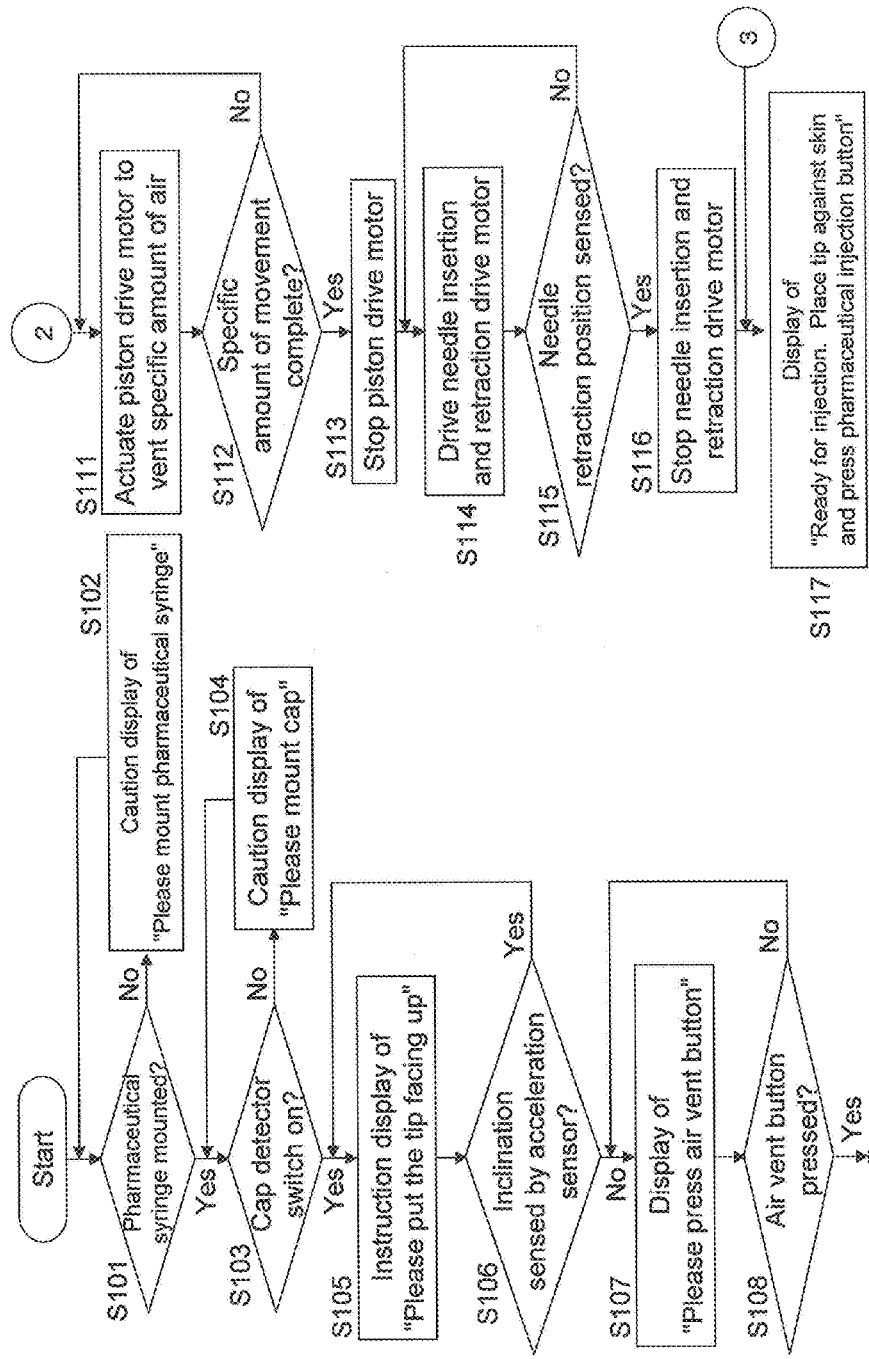
FIGS. 17a and 17b are flowcharts of the operational control of the pharmaceutical injection device in another embodiment of the present invention.

As shown in FIG. 17a, first, in step S101, it is determined whether or not the pharmaceutical syringe 4 has been mounted. If it has not been mounted, the flow proceeds to step S102, and a caution message of "Please mount the pharmaceutical syringe" is displayed on the display section 35. On the other hand, if the mounting of the pharmaceutical syringe 4 is detected, the flow proceeds to step S103.

Whether or not the pharmaceutical syringe 4 has been mounted may be accomplished by detecting the pharmaceutical syringe 4 directly, or it may be done indirectly as in Embodiment 1 above, by using the syringe cover detector switch 30 or the like to detect the syringe cover 25 covering the pharmaceutical syringe 4, for example.

Next, in step S103, the distal end cap detector switch 28 determines whether or not the distal end cap 23 has been mounted. If it has not been mounted, in step S104 a caution message of "Please mount the cap" is displayed on the display section 35.

With the pharmaceutical injection device in this embodiment, in the mounting determination of S101 and S103, the subsequent operation is not performed if the pharmaceutical syringe 4 and the distal end cap 23 have not been mounted.

Here, the distal end cap 23 is mounted to the distal end of the pharmaceutical injection device, serves as the part that goes against the skin during pharmaceutical injection, and has a stabilizing function of keeping the needle insertion depth constant when the injection needle 14 is inserted.

Next, if it is confirmed in S101 and S103 that the pharmaceutical syringe 4 and the distal end cap 23 have been mounted, then in S105 a display of "Please put the tip facing up" is left on the display section 35 for a specific length of time.

Then, in S106, the acceleration sensor 8 senses the inclination of the main body case 2.

The inclination discussed below will be referred to by using the direction perpendicular to the horizontal plane (the vertical direction) as zero degrees.

The acceleration sensor 8 also serves as an orientation sensor, and detects whether or not the distal end side of the pharmaceutical injection device (the side on which the injection needle 14 is mounted) is facing up.

This is to vent the air inside the pharmaceutical syringe 4 and the injection needle 14, and since air is lighter than the pharmaceuticals, if the distal end side is raised above horizontal, the air will be discharged from the tip of the injection needle 14. Preferably, it is recommended that the tip be within ±45 degrees (that is, a range of from −45 to +45 degrees) with respect to the vertical direction, and more preferably ±30 degrees (−30 to +30 degrees) with respect to the vertical direction. This allows the air inside the pharmaceutical syringe 4 and the injection needle 14 to escape faster and more reliably.

The flow does not proceed to the next step until it is detected that the distal end side of the pharmaceutical injection device has been tilted by a specific amount (in this case, within ±30 degrees with respect to the vertical direction). That is, if it is detected that the inclination is within ±30 degrees with respect to the vertical direction, the flow proceeds to step S107.

Next, in step S107, a message of "Please press the air vent button" is displayed on the display section 35.

Then, in step S108, it is determined whether or not the air vent button (not shown; may instead be another button) has been pressed, and the flow does not proceed to the next step until the air vent button has been pressed. Once the air vent button is pressed, the flow proceeds to step S111 shown in FIG. 17b.

Next, as shown in FIG. 17b, in step S111, the piston drive motor 10 is actuated to vent a specific amount of air.

Then, in step S112, the piston drive motor 10 is driven until the piston 5 has moved by a specific amount.

Consequently, the air inside the pharmaceutical syringe 4 and the injection needle 14 is discharged from the tip of the injection needle 14.

Next, in step S113, the piston drive motor 10 is stopped after it is detected that the piston 5 has moved by a specific amount in step S112.

Then, in step S114, the needle insertion and retraction drive motor 12 is driven to move the pharmaceutical syringe mounting portion 3 to the needle retraction position.

Then, in step S115, when the needle retraction position is detected, the flow proceeds to step S116.

Then, in step S116, the needle insertion and retraction drive motor 12 is stopped after the needle retraction position has been detected in step S115.

Then, in step S117, the display section 35 displays a message of "Ready for injection. Place tip against skin and press pharmaceutical injection button."

At this point, the user places the distal end cap 23 side of the pharmaceutical injection device against his skin and holds the pharmaceutical injection device there.

Figure 18B:
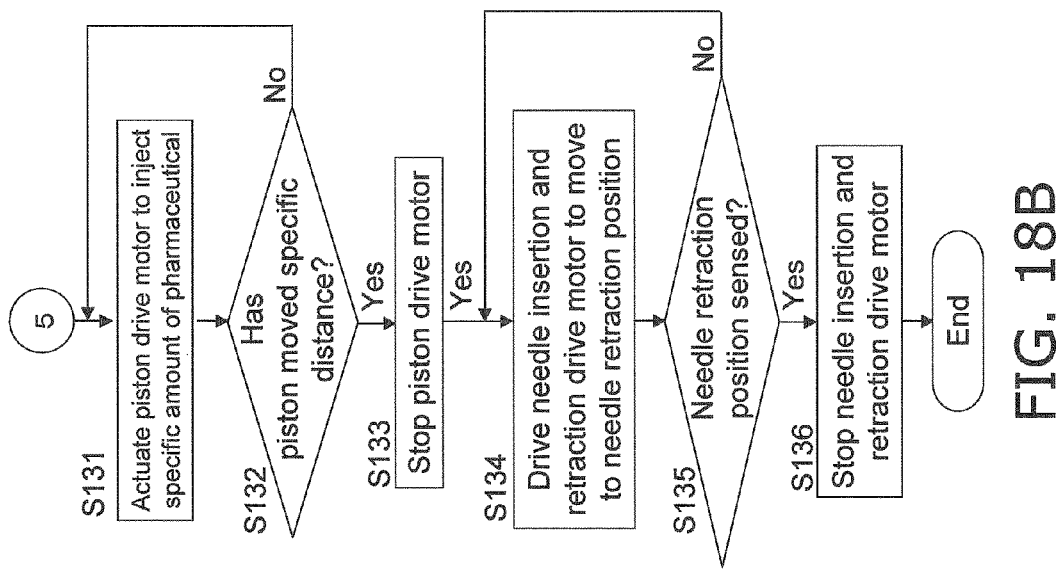
FIGS. 18a and 18b are flowcharts of the operational control of the pharmaceutical injection device in another embodiment of the present invention.
Figure 18A:
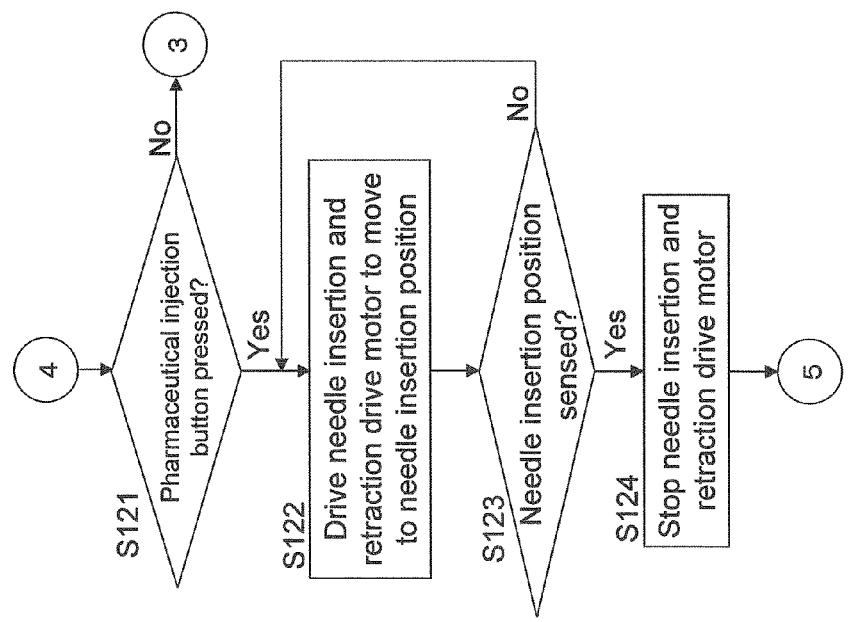

Then, as shown in FIG. 18a, in step S121, it is confirmed whether or not the pharmaceutical injection button 33 has been pressed. If the pharmaceutical injection button 33 has not been pressed, the flow returns to the above-mentioned step S117. If, however, the pharmaceutical injection button 33 has been pressed, the flow proceeds to step S122.

Then, in step S122, the needle insertion and retraction drive motor 12 is driven to move the pharmaceutical syringe mounting portion 3 to the needle insertion position.

Then, in step S123, it is determined whether or not the pharmaceutical syringe mounting portion 3 has moved to the needle insertion position. If it is detected here that the pharmaceutical syringe mounting portion 3 has moved to the needle insertion position, the flow proceeds to step S124.

At this point, the injection needle 14 disposed on the inside of the distal end cap 23 that is placed against the skin pops out and pierces the skin.

Then, in step S124, the needle insertion and retraction drive motor 12 is stopped.

Next, as shown in FIG. 18b, in step S131, the piston drive motor 10 is actuated and a specific amount of pharmaceutical is injected from the pharmaceutical syringe 4.

Then, in step S132, it is determined whether or not the amount of movement of the piston 5 has reached a specific amount. If the amount of movement of the piston 5 has reached the specific amount, the flow proceeds to step S133.

Then, in step S133, the piston drive motor 10 is stopped.

Then, in step S134, the needle insertion and retraction drive motor 12 is driven to move the pharmaceutical syringe mounting portion 3 to the needle retraction position.

Then, in step S135, it is determined whether or not the pharmaceutical syringe mounting portion 3 has moved to the needle insertion position. If it is determined here that the pharmaceutical syringe mounting portion 3 has moved to the needle insertion position, the flow proceeds to step S136.

At this point, the injection needle 14 that was inserted into the skin is retracted.

Then, in step S136, the needle insertion and retraction drive motor 12 is stopped, and the pharmaceutical injection operation is concluded.

Other Embodiments (A)

In Embodiments 1 and 2 above, a pharmaceutical injection device was described in which the needle insertion and retraction operations were both performed automatically, but the present invention is not limited to this.

For example, the above-mentioned operation in air venting mode may be carried out by using a pharmaceutical injection device (see FIGS. 21 and 22) that has no needle insertion or retraction operation.

Figure 19:
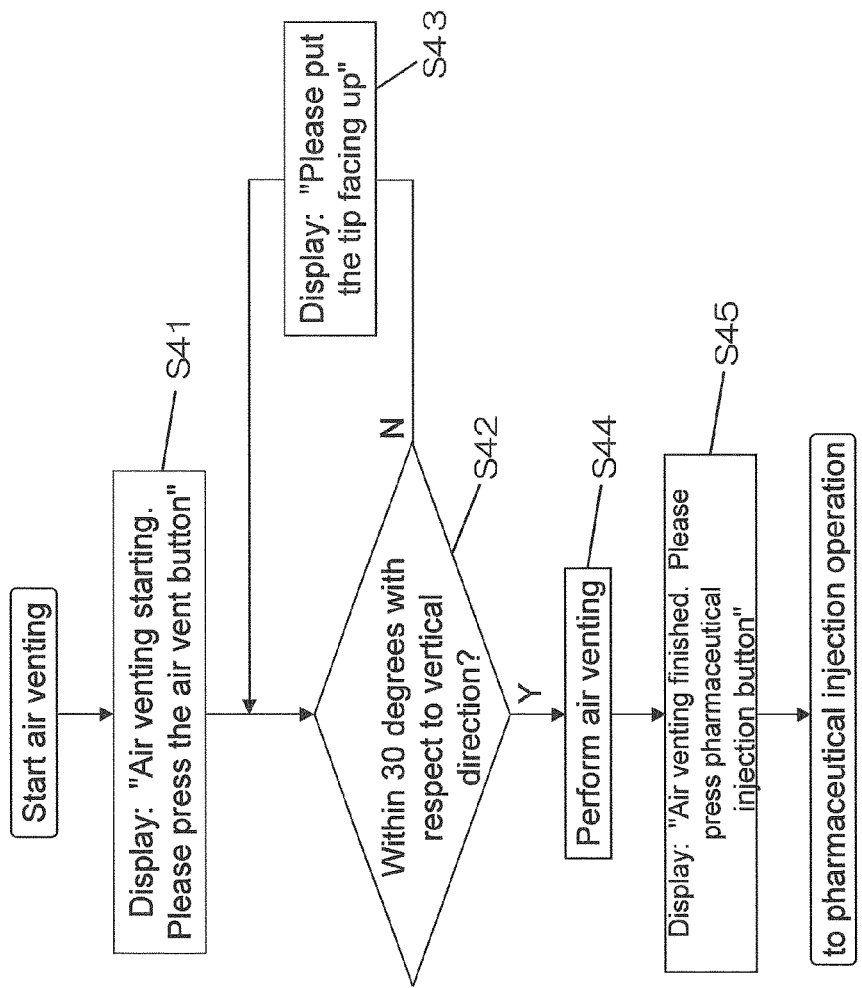
FIG. 19 is a flowchart of the operational control with the pharmaceutical injection device in yet another embodiment.

More specifically, the air venting operation may be performed after determining whether or not the air venting mode has been properly carried out according to the flow shown in FIG. 19.

Specifically, as shown in FIG. 19, when processing for air venting begins, first, in step S41 a message of "Air venting starting. Please press the air vent button" is displayed.

Then, in step S42, it is confirmed whether or not the distal end side of the pharmaceutical injection device is within a specific inclination (±30 degrees with respect to the vertical direction). If the answer is "Yes," the flow proceeds to step S44. If the answer is "No," on the other hand, the flow proceeds to step S43.

If the answer is "No" in step S42, a message of "Please put the tip facing up" is displayed in step S43. The flow then goes back to step S42, and it is confirmed whether or not the inclination angle is within a specific angle (±30 degrees with respect to the vertical direction in the example shown in FIG. 19).

On the other hand, if the answer is "Yes" in step S42, the air venting operation is performed in step S44.

Then, in step S45, a message of "Air venting finished. Please press pharmaceutical injection button" is displayed.

After this, the flow moves to the above-mentioned pharmaceutical injection operation.

Figure 20:
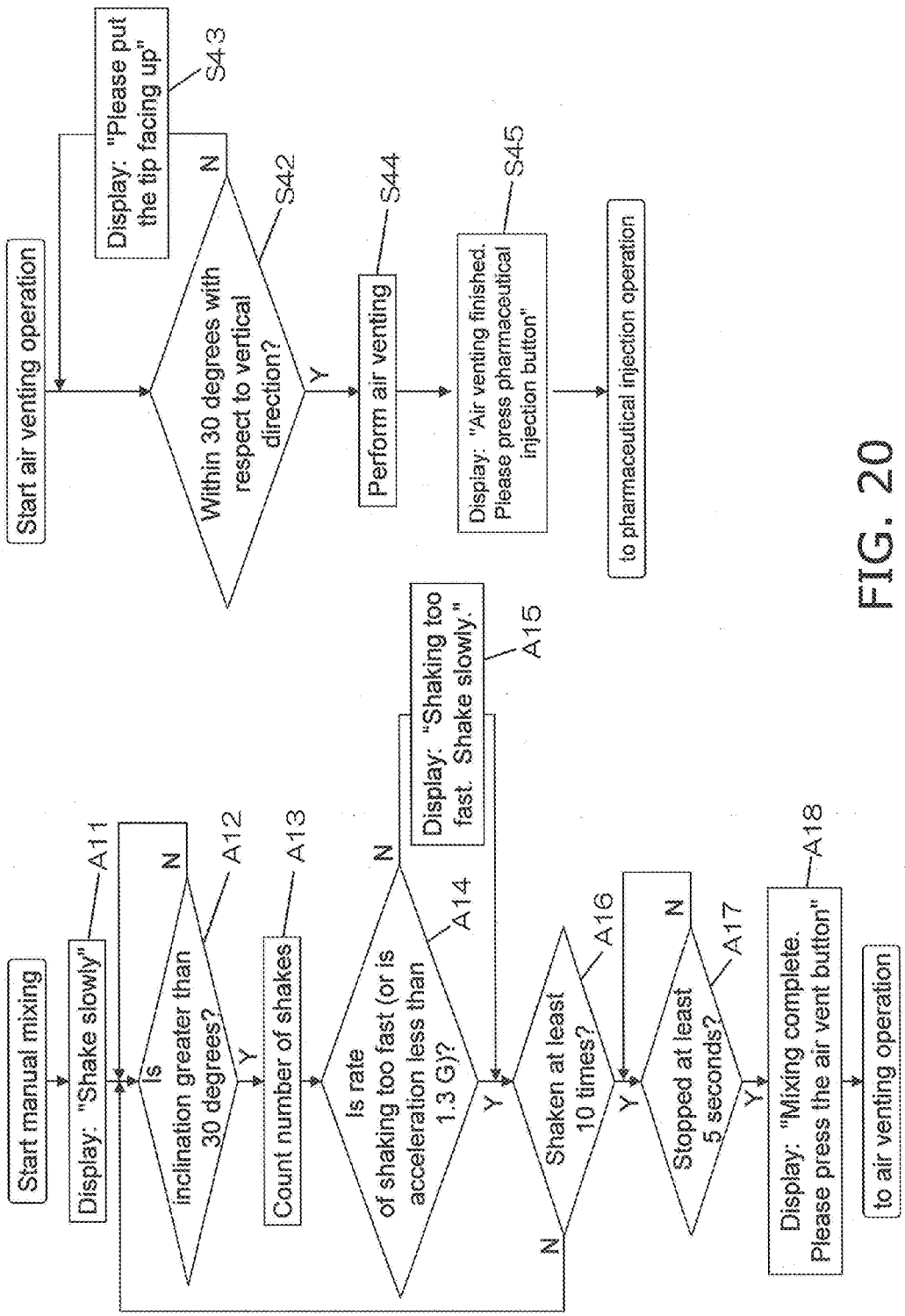
FIG. 20 is a flowchart of the pharmaceutical mixing and air venting operations performed in the flow shown in FIG. 19.

Consequently, even in air venting that does not involve needle insertion and retraction, the acceleration sensor 8 and the orientation detecting section 39 of the pharmaceutical injection device sense the inclination angle, and air venting cannot be performed as long as the inclination is not greater than a specific angle (30 degrees in the example shown in FIG. 20). Accordingly, the air venting operation can be carried out effectively and properly.

The flow when this air venting operation is performed in combination with a manual mixing operation will now be described through reference to FIG. 20.

Steps A11 to A16 are the same as steps A1 to A6 shown in FIG. 16 and described in the above embodiment.

In step S17, it is confirmed that the device was shaken at or above a specific number of times in step A16 (10 times in the example shown in FIG. 20), after which it is determined whether or not this has stopped for at least a specific length of time (5 seconds in the example shown in FIG. 20). If the answer here is "Yes," the flow proceeds to step A18. If the answer is "No," on the other hand, in step A17, it is again confirmed whether or not there has been stoppage for at least a specific length of time (5 seconds).

That is, because the flow goes through step A17, waiting at least a specific length of time (5 seconds) after the pharmaceutical injection device was shaken at least a specific number of times (10 times) in step A16 is a condition for proceeding to the next step A18.

Then, in step A18, a message of "Mixing complete. Please press the air vent button" is displayed.

The air venting operation then begins.

More specifically, the processing is performed in the order to the steps S42 to S45 described above (the same as in FIG. 19), and the flow moves to the pharmaceutical injection operation.

Furthermore, if the device is capable of automatically mixing the pharmaceuticals, the needle insertion and retraction operations do not necessarily have to be performed automatically.

Figure 21:
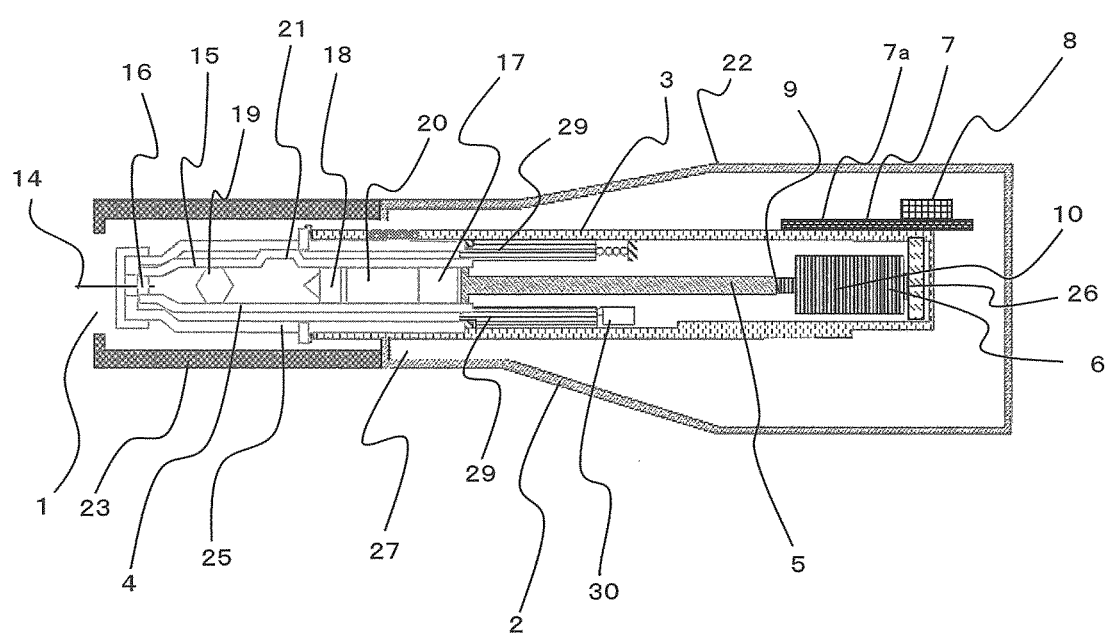
FIG. 21 is a cross section of the configuration of the pharmaceutical injection device pertaining to yet another embodiment of the present invention.

More specifically, as shown in FIG. 21, the pharmaceutical injection device may be one in which the needle insertion and retraction drive motor 12 is not installed in the main body case 2.

Figure 22:
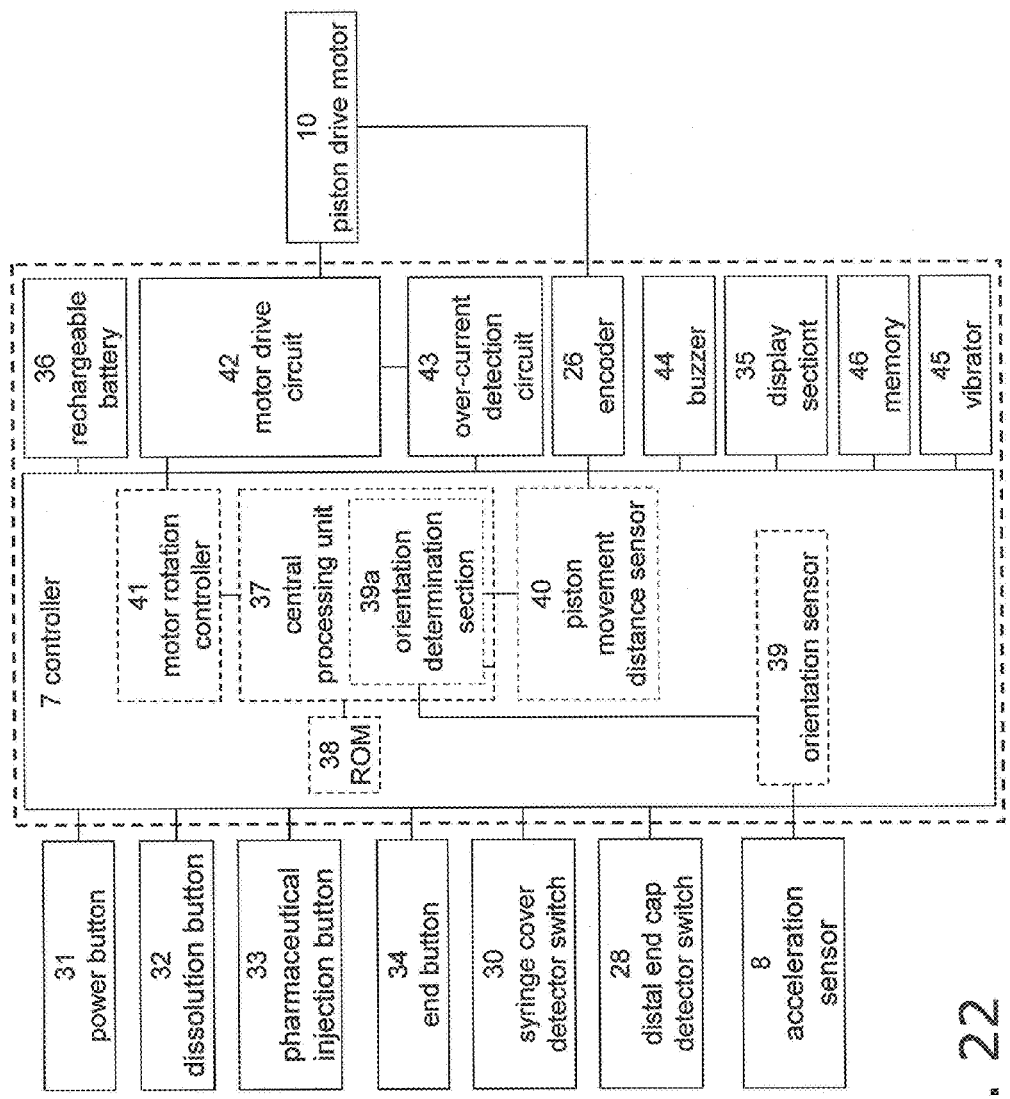
FIG. 22 is a control block diagram of the pharmaceutical injection device in FIG. 21.

More precisely, as opposed to the configuration shown in FIG. 2 and described in the above embodiment, with the configuration in FIGS. 21 and 22, there is no mechanism (the female threads 11, the needle insertion and retraction drive motor 12, and the bolt 13) for moving the pharmaceutical syringe mounting portion 3 back and forth through the opening 1.

Accordingly, with the pharmaceutical injection device shown in FIG. 21, upon completion of the pharmaceutical mixing and the air venting operations, and after the opening 1 side has been pressed against the needle insertion position, the needle insertion operation must be performed manually since there is no mechanism for making the tip of the injection needle 14 protrude from the opening 1 automatically.

That is, the present invention can of course also be applied to a semi-automatic pharmaceutical injection device such as this.

(B)

In the above embodiments, an example was given of a pharmaceutical injection device in which the pharmaceutical was injected by putting the pharmaceutical syringe 4 in place, mixing the pharmaceuticals, venting the air, and performing the pharmaceutical injection operation, but the present invention is not limited to this.

For instance, if the acceleration sensor 8 detects a malfunction during the pharmaceutical injection operation, control may be performed to bring about an emergency shutdown.

Figure 23:
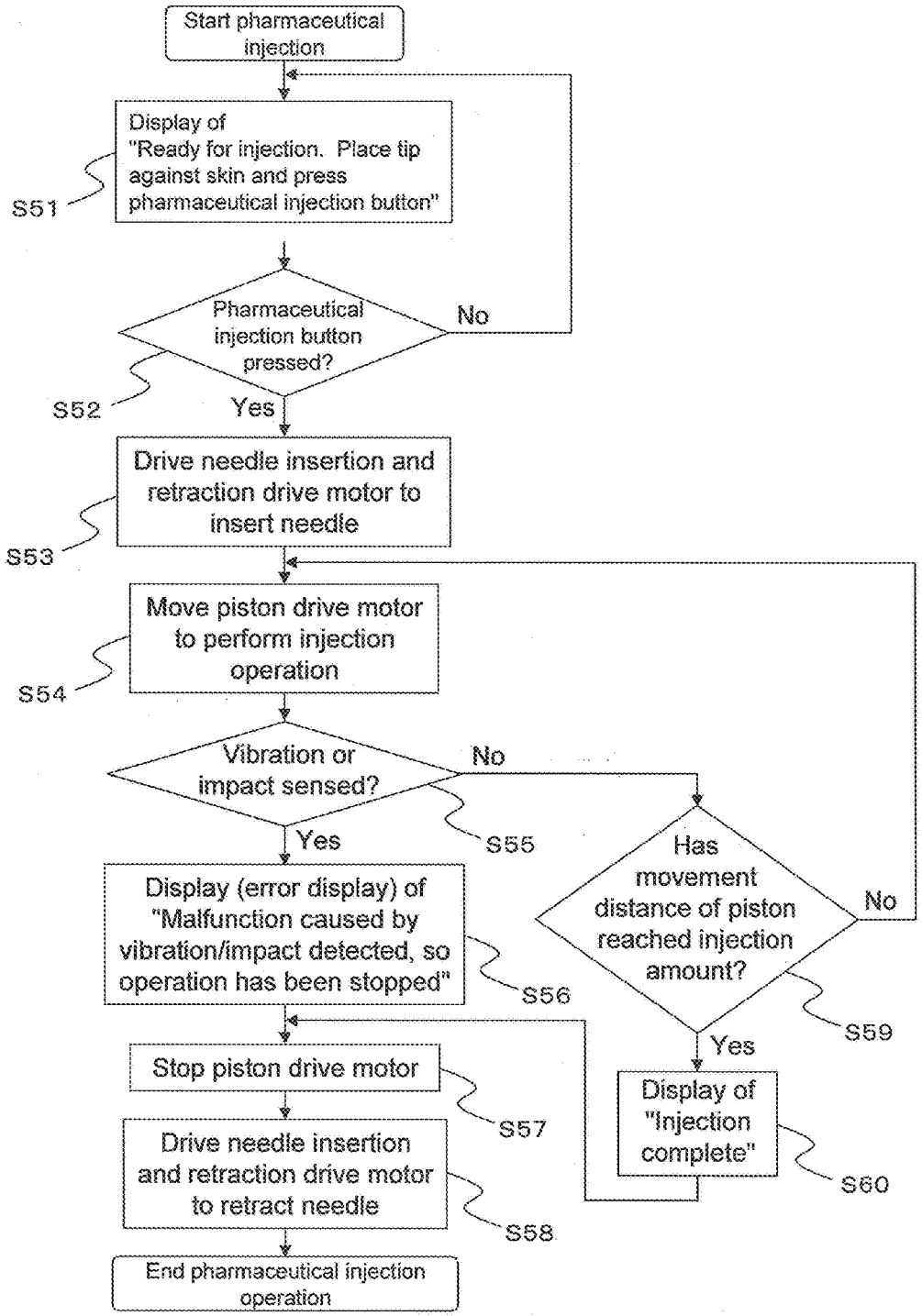
FIG. 23 is a flowchart of the operational control of the pharmaceutical injection device in yet another embodiment of the present invention.

More specifically, as shown in FIG. 23, when the pharmaceutical injection operation is started, first, in step S51, the display section 35 displays a message of "Ready for injection. Place tip against skin and press pharmaceutical injection button."

Then, in step S52, it is determined whether or not the pharmaceutical injection button 33 has been pressed. If the pharmaceutical injection button 33 has been pressed, the flow proceeds to step S53.

Then, in step S53, the needle insertion and retraction drive motor 12 is driven to perform needle insertion.

Then, in step S54, the piston drive motor 10 is driven to move the piston 5 and begin the injection of the pharmaceutical.

With the pharmaceutical injection device in this embodiment, the acceleration sensor 8 determines whether or not a malfunction has occurred during the pharmaceutical injection operation.

More specifically, in step S55, if the acceleration sensor 8 detects a malfunction such as vibration or impact to the pharmaceutical injection device during the pharmaceutical injection operation, the flow proceeds to step S56.

Then, in step S56, the display section 35 displays a caution message of "Malfunction caused by vibration/impact detected, so operation has been stopped."

Then, in step S57, the piston drive motor 10 is stopped, or the piston 5 is moved to its home position.

Then, in step S58, the needle insertion and retraction drive motor 12 is driven to perform the needle insertion operation.

Meanwhile, if the acceleration sensor 8 does not detect any malfunction such as vibration or shaking, the flow proceeds to steps S59 and S60 as the normal pharmaceutical injection operation.

In this case, in step S59, the piston drive motor 10 is driven until the movement distance of the piston 5 reaches a specific injection amount (pharmaceutical injection amount).

Then, in step S60, a display is given indicating a normal end to the injection operation, the flow proceeds to step S57, after the piston drive motor is stopped, and the needle insertion and retraction drive motor 12 is driven to perform the needle retraction operation, the pharmaceutical injection operation is concluded.

As discussed above, with the pharmaceutical injection device in this embodiment, when a malfunction such as vibration or shaking is detected by the acceleration sensor 8 during the pharmaceutical injection operation, control is performed to bring the pharmaceutical injection operation to an emergency shutdown for the sake of safety.

This affords a pharmaceutical injection device that is safer to use.

Naturally, with a pharmaceutical injection device having no needle insertion or retraction operation, the above-mentioned act of "driving the needle insertion and retraction drive motor 12 to perform the needle retraction operation" cannot be done, so this needle retraction operation is eliminated.

(C)

In the above embodiments, an example was given of a pharmaceutical injection device in which the pharmaceutical was injected by putting the pharmaceutical syringe 4 in place, mixing the pharmaceuticals, venting the air, and performing the pharmaceutical injection operation, but the present invention is not limited to this.

For instance, if, for some reason, the mixed pharmaceuticals should be left without being injected after the completion of the pharmaceutical mixing operation, the pharmaceuticals will have to be mixed again, so a second mixing operation may be performed as follows.

Figure 24:
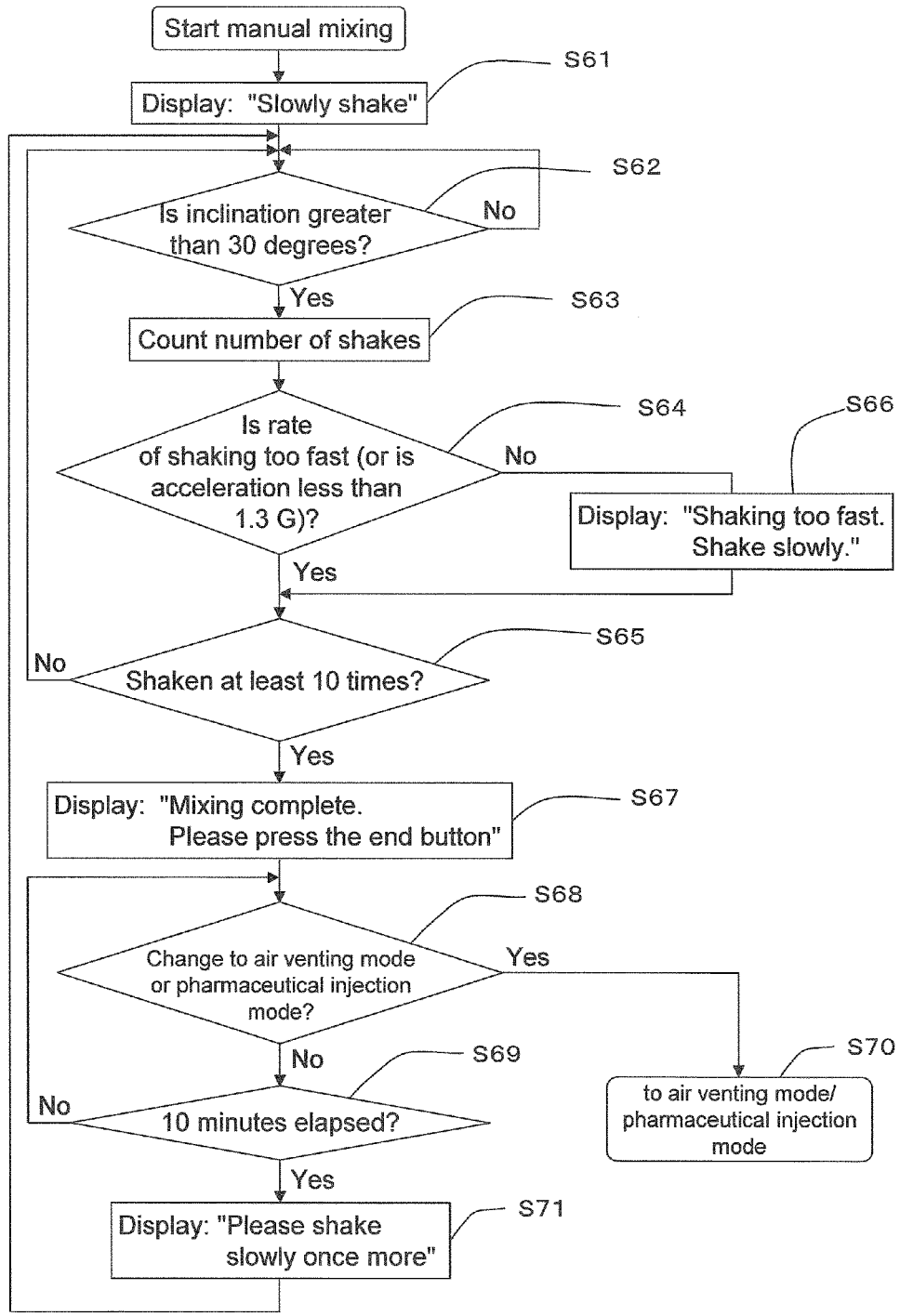
FIG. 24 is a flowchart of the operational control of the pharmaceutical injection device in yet another embodiment of the present invention.

As shown in FIG. 24, when the pharmaceutical injection operation is started, first, in step S61, the display section 35 displays a message of "Slowly shake."

Then, in step S62, it is determined whether or not the inclination is greater than a specific angle for mixing (30 degrees with respect to the vertical direction in the example shown in FIG. 24). If the inclination is greater than a specific angle for mixing (such as 30 degrees with respect to the vertical direction), the flow proceeds to step S63. On the other hand, if the inclination is at or below a specific angle for mixing (such as 30 degrees with respect to the vertical direction), step S62 is repeated.

Then, if it is determined in step S62 that the inclination of the pharmaceutical injection device is greater than 30 degrees, in step S63 the number of times the pharmaceutical injection device has been shaken is counted.

Then, in step S64, it is determined whether the shaking rate is too fast, or the acceleration is less than a specific amount for mixing (such as whether the acceleration is less than 1.3 G). If the acceleration is greater than 1.3 G, the flow proceeds to step S65. On the other hand, if the acceleration is at or below 1.3 G, the flow proceeds to step S66, and the display section 35 displays a message of "Shaking too fast. Shake slowly."

Then, in step S65, it is determined whether or not the number of shakes is at or above a specific number (such as 10 times). If it is determined that the device has been shaken at least a specific number of times (such as 10 times) for mixing, the flow proceeds to step S67, but if it is less than the specific number of times (such as 10 times) for mixing, the flow goes back to step S62.

Then, if it is determined in step S65 that the device has been shaken at least a specific number of times (such as 10 times) for mixing, the display section 35 displays a message of "Mixing complete. Please press the end button."

Then, in step S68, it is determined whether or not there has been a change to air venting mode or to pharmaceutical injection mode. If there has been a change, the flow proceeds to step S69. If there has not been a change, the flow proceeds to step S70, and the mode is changed to air venting mode or pharmaceutical injection mode.

Then, in step S69, it is determined whether or not at least the specific time (such as 10 minutes) required for remixing after pharmaceutical mixing operation has elapsed. If the specific time (such as 10 minutes) required for remixing has elapsed, the flow proceeds to step S71. On the other hand, if the specific time (such as 10 minutes) required for remixing has not elapsed, the flow goes back to step S68, and it is again determined whether or not there has been a change to air venting mode or pharmaceutical injection mode.

Then, in step S71, the display section 35 displays a message of "Please shake slowly once more," and the flow goes back to step S62 and the mixing operation is performed again.

As discussed above, with the pharmaceutical injection device in this embodiment, when there has been no change to the air venting mode or pharmaceutical injection mode after completion of the pharmaceutical mixing operation, it is concluded that the pharmaceutical has been left standing for at least a specific length of time, and a message recommending remixing is displayed.

Consequently, this prevents the user from using a pharmaceutical injection device that for some reason has been left standing in the same state as at the completion of the pharmaceutical mixing operation, and accidentally injecting a pharmaceutical that may not be thoroughly mixed.

Furthermore, the pharmaceutical that is to be remixed is not limited to the pharmaceutical including a plurality of formulations (such as the above-mentioned solid pharmaceutical 19 and liquid pharmaceutical 20). For example, there are pharmaceuticals that will separate and settle when left standing for an extended period of time, even with single-liquid formulations, so in such cases the present invention is applicable in that mixing has to be performed again.

(D)

Figure 25:
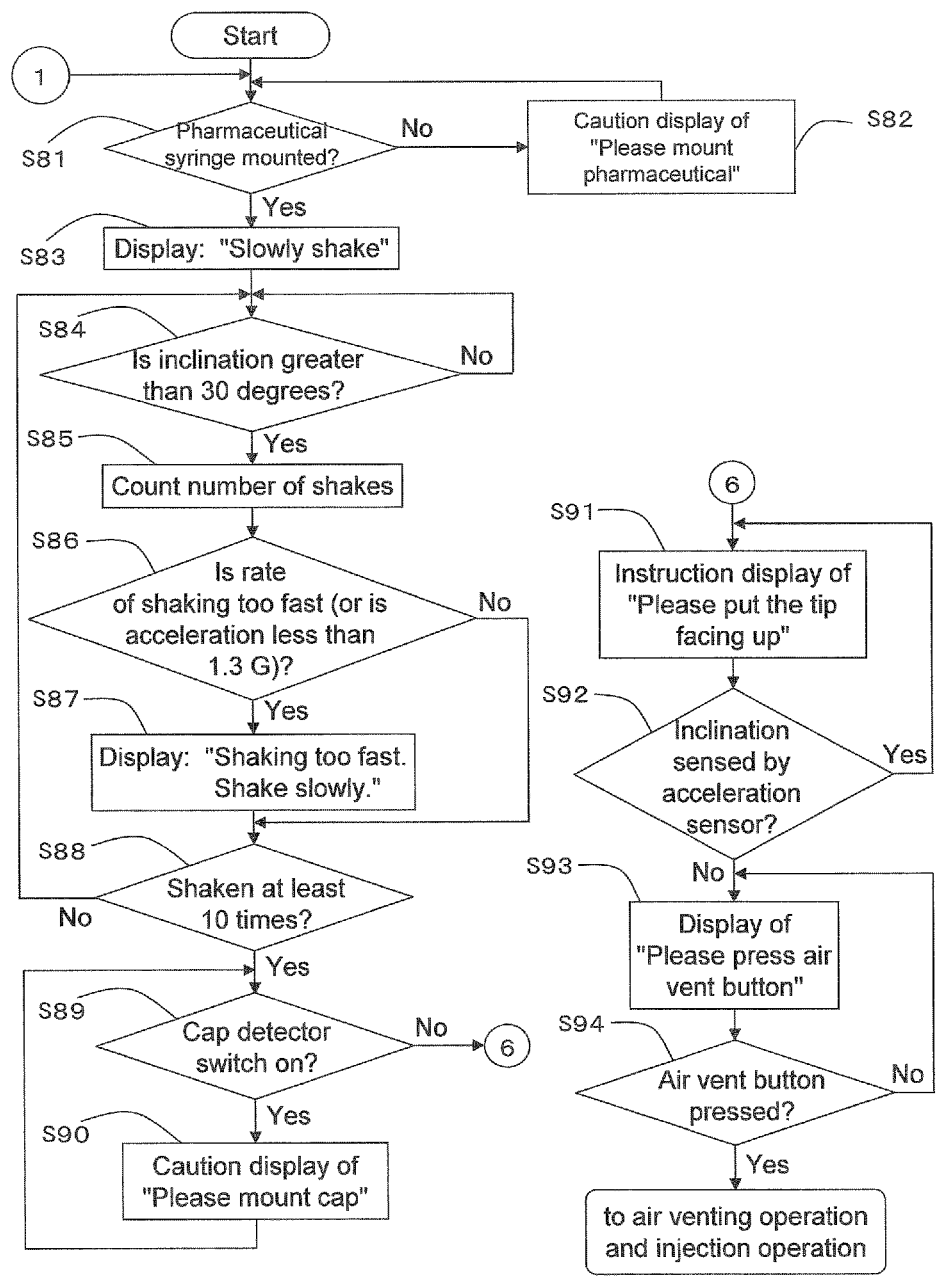
FIG. 25 is a flowchart of the operational control with the pharmaceutical injection device in yet another embodiment.

The above-mentioned remixing operation was performed according to how much time had elapsed since the mixing operation, but as shown in FIG. 25, it is also possible to perform the mixing operation every time the pharmaceutical in the pharmaceutical syringe is injected.

The reason for this is that pharmaceuticals that need this remixing may separate and settle if allowed to stand for a certain amount of time.

In FIG. 25, after the mounting of the pharmaceutical syringe has been confirmed (step S81), a message recommending manual mixing is displayed (step S82), and the manual mixing operation described above is performed (see the description for FIG. 20 above).

Here, manual mixing is done every time the pharmaceutical syringe is mounted, but this is not necessarily the only option, and it is also possible to perform the mixing operation after first visually checking the mixing state after the mounting of the pharmaceutical syringe.

In this case, if it is decided after visual confirmation that mixing is necessary, the manual mixing operation (steps S83 to S88) are commenced by pressing the "start button" (not shown) (may be another button instead).

After the completion of this manual mixing operation (S88), the flow moves to the above-mentioned air venting operation and pharmaceutical injection operation.

(E)

In the above embodiments, as shown in FIG. 5, an example was given of a pharmaceutical mixing operation that included an air venting mode, but the present invention is not limited to this.

For example, it should go without saying that the pharmaceutical injection device of the present invention can also be applied to the mixing of pharmaceuticals in which there is no air venting mode.

(F)

In the above embodiments, an example was given of the configuration of a pharmaceutical injection device when two pharmaceuticals (the solid pharmaceutical 19 and the liquid pharmaceutical 20) were dissolved and mixed, but the present invention is not limited to this.

For example, the same effect as in the above embodiments can be obtained with the pharmaceutical injection device of the present invention when a single pharmaceutical is used and is remixed in the event of its separation, the settling of crystals, and so forth.

INDUSTRIAL APPLICABILITY

As discussed above, with the pharmaceutical injection device of the present invention, mixing is performed by shaking the main body case in the manual mixing mode of the pharmaceutical syringe, and pharmaceutical injection can be performed after the proper mixing state has been achieved by tilting the main body case to an inclination angle that is greater than a specific value, and therefore the present invention is expected to find wide application in the field of pharmaceutical injection devices and the like that require the mixing of a pharmaceutical or pharmaceuticals.

The invention claimed is:

1. A pharmaceutical injection device, comprising:
    a main body case including an opening;
    an injection needle configured to be inserted and retracted through the opening;
    a pharmaceutical syringe mounting portion provided inside the main body case;
    a pharmaceutical syringe mounted to the pharmaceutical syringe mounting portion;
    a piston movable in respect to the pharmaceutical syringe;
    a drive mechanism configured to drive the piston;
    an orientation sensor configured to sense an inclination angle of the main body case;
    a controller electrically connected to the drive mechanism and the orientation sensor, the controller configured to execute a plurality of modes in a sequence,
    the plurality of modes including a manual mixing mode;
    wherein when the manual mixing mode is selected, the controller is configured to change the mode to a next mode when the inclination angle is greater than a specific value.

2. The pharmaceutical injection device according to claim 1, wherein:
    when the manual mixing mode is selected, the controller is further configured to count a number of times that the inclination angle has been greater than a threshold angle, and
    the controller changes the mode to the next mode if the number of times is greater than or equal to a threshold number of times.

3. The pharmaceutical injection device according to claim 2, wherein:
    the orientation sensor includes an acceleration sensor configured to sense an acceleration, and the inclination angle, of the main body case when manual mixing mode is selected.

4. The pharmaceutical injection device according to claim 1, wherein:
    the orientation sensor includes an acceleration sensor configured to sense an acceleration, and the inclination angle, of the main body case when manual mixing mode is selected.

5. The pharmaceutical injection device according to claim 4, further comprising:
    a display section connected to the controller;
    wherein the controller causes the display section to display a message prompting the user to minimize shaking of the main body case when the acceleration sensed by the acceleration sensor is greater than a threshold acceleration.

6. The pharmaceutical injection device according to claim 1, wherein:
    the pharmaceutical syringe includes:
        a cylinder,
        a distal end gasket provided on a distal end side inside the cylinder,
        a push-in gasket provided on a rear end side inside the cylinder,
        a separation gasket provided-between the distal end gasket and the push-in gasket,
        a solid pharmaceutical contained inside the cylinder between the distal end gasket and the separation gasket,
        a liquid pharmaceutical contained inside the cylinder between the push-in gasket and the separation gasket, and
        a bypass that protrudes in an outer peripheral direction of the cylinder at a portion of the cylinder between the distal end gasket and the separation gasket.

7. The pharmaceutical injection device according to claim 1, wherein:
    the controller changes the mode to the manual mixing mode after performing an automatic dissolution operation,
    the automatic dissolution operation including mixing and dissolving two pharmaceuticals housed in the pharmaceutical syringe.

8. The pharmaceutical injection device according to claim 1, wherein:
    the controller changes the mode to the manual mixing mode prior to a pharmaceutical injection operation.

9. The pharmaceutical injection device according to claim 1, wherein:
    the next mode is an air venting mode.

10. The pharmaceutical injection device according to claim 1, wherein:
    the controller is configured to change the mode to the manual mixing mode more than once after performing an automatic dissolution operation and prior to an pharmaceutical injection operation.

* * * * *